(12) United States Patent
Madder et al.

(10) Patent No.: US 9,290,537 B2
(45) Date of Patent: Mar. 22, 2016

(54) METHOD FOR CROSS-LINKING PEPTIDES

(75) Inventors: Annemieke Madder, B-Massemen (BE); Kurt Hoogewijs, Overmere (BE); Annelies Deceuninck, Ghent (BE); Lieselot Carrette, Beernem (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 13/996,583

(22) PCT Filed: Dec. 23, 2011

(86) PCT No.: PCT/EP2011/073974
§ 371 (c)(1),
(2), (4) Date: Jun. 21, 2013

(87) PCT Pub. No.: WO2012/085279
PCT Pub. Date: Jun. 28, 2012

(65) Prior Publication Data
US 2013/0289239 A1    Oct. 31, 2013

(30) Foreign Application Priority Data
Dec. 23, 2010   (EP) .................................... 10196898

(51) Int. Cl.
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| C07K 1/107 | (2006.01) |
| C07K 1/00 | (2006.01) |
| C07K 1/13 | (2006.01) |

(52) U.S. Cl.
CPC ............... *C07K 1/1075* (2013.01); *C07K 1/006* (2013.01); *C07K 1/1077* (2013.01); *C07K 1/13* (2013.01)

(58) Field of Classification Search
None
See application file for complete search history.

(56) References Cited

U.S. PATENT DOCUMENTS

| 7,410,761 B2 * | 8/2008 | Williams ........... C12N 15/1034 435/6.12 |
| 7,488,600 B2 * | 2/2009 | Williams ........... C12N 15/1034 435/440 |
| 2004/0162242 A1 | 8/2004 | Olson et al. |
| 2005/0222088 A1 * | 10/2005 | Chakraborty ........ C07D 307/68 514/63 |
| 2006/0183888 A1 | 8/2006 | Chan et al. |

FOREIGN PATENT DOCUMENTS

WO    WO 99/47154 A1    9/1999

OTHER PUBLICATIONS

Tian, Zhen-ping, et al. Structure-activity studies of LH-RH antagonists with side-chain modified D-lysine in position 6, Pept.: Biol. Chem., Proc. Chin. Pept. Symp. 1993. Meeting Date 1992, pp. 45-48.*

Deceuninck, et al: Oral Presentations—S17-5: Biomimetic furan oxidation: a 'trojan horse' strategy for crosslinking and labeling of peptides; J Peptide Sci; Jan. 1, 2008, vol. 14, No. S1, pp. 10-45.

Deceuninck, et al: From DNA cross-linking to peptide labeling: on the versatility of the furan-oxidation-conjugation strategy; Chemical Communications; Jan. 2009, No. 3, pp. 340-342.

SINZ: Chemical Cross-Linking and Mass Spectrometry to Map Three-Dimensional Protein Structures and Protein-Protein Interactions; Bioconjugate Chemistry; Jul. 1, 2006, vol. 25, No. 4, pp. 663-682.

Zhu, et al: Covalent Cross-Linking of Glutathione and Carnosine to Proteins by 4-Oxo-2-nonenal; Chem Res Tox; Jun. 15, 2009; vol. 22, No. 6, pp. 1050-1059.

International Preliminary Report on Patentability, PCT/EP2011/073974; date of report Jun. 25, 2013, 11 pages.

* cited by examiner

*Primary Examiner* — Marcela M Cordero Garcia
(74) *Attorney, Agent, or Firm* — James H. Velema, Esq.; Lathrop & Gage, LLP

(57) ABSTRACT

The present invention relates to a method for cross-linking peptides using an activated furan-moiety. In particular, the present invention provides a method for cross-linking peptides comprising the steps of: a) providing a composition comprising furan-peptides, said furan-peptides comprising at least one amino acid comprising a furan-moiety; b) contacting said composition comprising furan-peptides with second peptides, thereby obtaining a mixture comprising furan-peptides and second peptides; c) adding an activation signal to said mixture of step b), thereby activating said furan-peptides to activated furan-peptides, and d) reacting said activated furan-peptides with said second peptides, thereby cross-linking said activated furan-peptides with said second peptides.

28 Claims, 18 Drawing Sheets

SEQ ID NO: 27

SEQ ID NO: 28

SEQ ID NO: 29

SEQ ID NO: 30

SEQ ID NO: 31

METHOD FOR CROSS-LINKING PEPTIDES

RELATED APPLICATIONS

This application is a 35 U.S.C. §371 filing of International Application No. PCT/EP2011/073974, filed Dec. 23, 2011; which claims priority to European Patent Application No. 10196898.0, filed on Dec. 23, 2010. The entire contents of each are incorporated herein by reference.

SEQUENCE LISTING

The instant application contains a Sequence Listing which has been submitted electronically in ASCII format and is hereby incorporated by reference in its entirety. Said ASCII copy, created on Jul. 17, 2015, is named 548255DCV-002US SL.txt and is 12,738 bytes in size.

FIELD OF THE INVENTION

The present invention relates to a method for cross-linking peptides using an activated furan-moiety.

BACKGROUND OF THE INVENTION

Many signals are perceived by cells via ligand-receptor interactions at the interface between their plasma membranes and their micro-environment. Such communications relay diverse cues about development, nutrient availability or the presence of pathogens. Their importance is highlighted by the fact that membrane receptors are major drug targets. The activation of receptors by their cognate ligands is based on their reversible interaction, thereby forming a transient complex. The study of this complex is at the core of important research fields, including drug discovery. Classical methods for the study of protein-protein or ligand-receptor are generally laborious and often limited by the large amount of biological material required for analysis (X-ray diffraction, crystallography, mass spectrometry), the limited mass range (NMR-spectroscopy), the low-specificity (ultracentrifugation) or the low mass resolution (gel electrophoresis). An additional intrinsic problem in the characterization of non-covalently bound assemblies is that their analysis generally leads to the disruption of the weak and transient interactions. Hence, alternative or improved approaches that combine speed, accuracy and sensitivity for the detection of ligand-receptor interactions are actively sought after.

Chemical cross-linking results in the formation of artificial covalent bonds between the close interacting partners. It is a powerful method because it locks together receptors and their ligands normally associated only by weak and transient interactions, thereby enabling a wide range of analytical techniques that disrupt non-covalent bonds. Indeed, cross-linking techniques are nowadays extensively used for many proteomics methods including the analysis of protein structure and interactions, and for therapeutic use. Identifying unknown binding partners and specific interaction sites are among the most intense research.

Among the oldest cross-linking reagents are formaldehyde and glutaraldehyde. Due to their small size, they can penetrate through cell walls where they form cross-links between both proteins and nucleic acids, making them still one of the most efficient cross-linkers. However, glutaraldehyde and formaldehyde based cross-linking is not specific, resulting in many different complex products and modifications of the starting material. As a result, the cross-linked adducts are difficult to analyze, making the biological relevance of this cross-linking technique questionable.

More modern cross-link techniques take advantage of functional groups of which the intrinsic reactivity is only triggered by an external signal, such as light-irradiation. However, these functional groups are normally very bulky, disrupting normal protein-protein interactions or cannot be easily incorporated into a protein. Moreover, photo-activation cross-link techniques result on average in low cross-link yields and damage of the peptides under study. The smaller photo-reactive groups such as phenylazide, phenyldiazirine and benzophenone have major drawbacks. For instance, the phenylazide probes produce various by-products; the phenyldiazirine is only accessible through extensive and costly synthesis; and the benzophenone probe requires prolonged UV-irradiation, damaging and non-specifically cross-linking the starting material.

Although furan is commercially available, its use has always been limited in view of its toxicity and carcinogenicity. In the liver, cytochrome P450 catalyzes oxidation of furan to a reactive aldehyde, which subsequently reacts with sulfhydryl and amine groups.

WO 2010/068278 relates to the production of carrier-peptide conjugates through reaction between two chemically reactive unnatural amino acids. Thus, in this highly artificial system both binding partners must have unnatural amino acids, opposing the study of any natural protein-protein interaction.

Stevens and Madder describe furan-modified oligonucleotides for fast high-yielding and site selective DNA inter-strand cross-linking with non-modified complements (Stevens and Madder, *Nucleic Acids Research*, 2009, vol. 37(5), 1555-1565). Although the distances within the major and minor groove in the DNA duplex are known and fixed, and although the complementary (binding) nucleotides are known, Stevens and Madder describe a strong selectivity for cross-linking to either complementary A or C. In contrast, proteins are exceedingly more complex in each dimension, e.g. by the number of building blocks, conformations, cis-interactions, trans-interactions, transient interactions, anonymity of the binding partner, etc. Obviously, Stevens and Madder are completely silent on cross-linking of proteins.

Deceuninck et al. describe a strategy for peptide labeling on a solid support, relying on the incorporation of a furan moiety (Deceuninck et al., *Chem. Commun.*, 2009, 21(3), 340-342). However, already the first step of providing peptides comprising a furan-moiety is arduous. Indeed, only after linking the dye to the peptide, the labeled peptide was cleaved from the solid support on which the peptide was synthesized. Schulz et al. (*Protein and Peptide Letters*, 2004, 11, 601-606) underscore the difficulties in achieving substantially pure furan-peptides by Fmoc-based solid phase synthesis. Apparently, Deceuninck et al. is wholly silent on protein-protein interactions.

N-bromo-succinimide (NBS) can be used for selective oxidation of furan rings, e.g. in site selective DNA inter-strand cross-linking (see Stevens and Madder ibid.). However, the use of NBS for selectively oxidizing peptides comprising a furan-moiety is counter intuitive, considering the sensitivity of various amino acids to oxidize as well as the known use of NBS to degrade proteins.

Therefore, there remains a need in the art to provide improved methods for cross-linking peptides. In addition, there remains a need in the art to improve methods for providing free furan-peptides.

SUMMARY OF THE INVENTION

The present inventors have found a method for cross-linking peptides overcoming one or more of the above-mentioned problems of the prior art. The present invention relates to methods for cross-linking peptides comprising the steps of: a) providing a composition comprising furan-peptides, said furan-peptides comprising at least one amino acid comprising a furan-moiety; b) contacting said composition comprising furan-peptides with second peptides, thereby obtaining a mixture comprising furan-peptides and second peptides; c) adding an activation signal to said mixture of step b), thereby activating said furan-peptides to activated furan-peptides, and d) reacting said activated furan-peptides with said second peptides, thereby cross-linking said activated furan-peptides with said second peptides.

The inventors have found that the methods of the present invention allow cross-linking of a peptide with a known or unknown second peptide, with high efficiency and specificity. Since the methods of the present invention allow cross-linking of a peptide with an unknown second peptide, they have the advantage that they enable the identification of unknown binding partners. Furthermore, the methods of the present invention allow cross-linking of two interacting peptides and identifying a binding site between the peptides.

In addition, cross-linking of peptides according to the methods of the present invention is efficient and results in high yields of cross-linked products. Moreover, the methods of the invention allow activation of the cross-link through the addition of a nondestructive activation signal, thereby advantageously preventing damage to the peptides under study.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

BRIEF DESCRIPTION OF THE FIGURES

FIG. 8 discloses SEQ ID NOs 20, 21, 21 and 2, respectively, in order of appearance.

FIG. 9 discloses SEQ ID NOs 22, 22, 22 and 3, respectively, in order of appearance.

FIG. 10 discloses SEQ ID NOs 20 and 2, respectively, in order of appearance.

FIG. 11 discloses SEQ ID NO: 4.

FIG. 12 discloses SEQ ID NO: 4.

FIG. 13 discloses SEQ ID NO: 1.

FIG. 18 discloses SEQ ID NO: 23.

FIG. 19 discloses SEQ ID NOs 24, 6 and 6, respectively, in order of appearance.

FIG. 20 discloses SEQ ID NOs 25 and 26, respectively, in order of appearance.

FIG. 21 discloses SEQ ID NOs 27-31, respectively, in order of appearance.

FIG. 22 discloses SEQ ID NOs 32-35, respectively, in order of appearance.

DETAILED DESCRIPTION OF THE INVENTION

Figure 1:
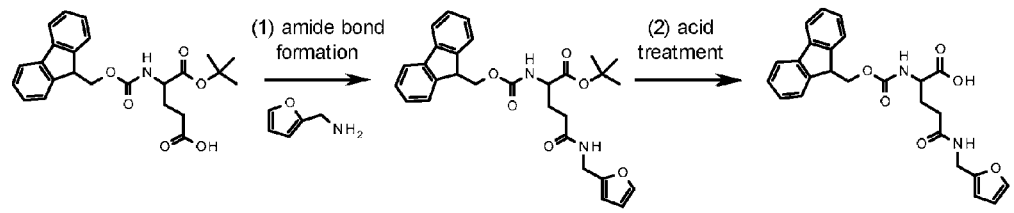
FIG. 1 schematically represents the synthesis of a furan amino acid from a commercially available furyl amine derivative and a glutamic acid derivative. (1): amide bond formation; (2): acid treatment.

Before the present method and products of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

A problem in studying protein-protein interactions is the transient contact of the binding partners. Current cross-linking techniques are unsatisfactory since they are unspecific, low-yielding, costly and/or destructive.

The present inventors realized, contrary to general belief, that furan-peptides may be excellent candidates for selectively and specifically cross-linking binding partners.

The present invention concerns realizing and reducing to practise the specific incorporation of a furan moiety into a peptide and its further selective conversion into a reactive enal functionality. This electrophilic moiety can be easily attacked by nucleophiles and can so be used for cross-linking purposes. The present invention realized (1) site-selective introduction of the furan moiety at any desired position in a furan-peptide; (2) maintaining the conformation and activity of the peptide; (3) maintaining the furan moiety in a non-reactive status, which is only transformed into a reactive moiety upon use of a triggering or activation signal; (4) the use of a triggering signal which is specific and/or non-destructive; and/or (5) cross-linking the binding partners specifically, and limited and localized to binding sites which are in close contact.

In particular, the furan-oxidation cross-link technique leads to the generation of covalently connected peptide-peptide complexes. This cross-linking is used in target identification procedures and studies of multimeric protein complexes for the elucidation of the complex protein machinery behind biological phenomena. An important advantage of the presented method is the possibility to generate the reactive cross-link functionality only after formation of the complex under study. Indeed, the mere conversion, in aqueous medium, of an easily incorporated unreactive furan into a very reactive functional group holds great promise in this context. In comparison with other reactive probes that can be incorporated into biomolecules, the furan moiety possesses inducible reactivity and is only transformed into a reactive moiety upon a triggering signal (chemical or enzymatic). Collateral damage to non-targets in this way remains minimal. A further attractive feature of the furan-oxidation triggered cross-link reaction is the high yield of isolated cross-linked products, this in contrast to the on average low cross-link yields reported for photoreactive probes. Next, cross-linking techniques based on photoactivatable probes require intense UV-irradiation for activation which can lead to damage of the proteins under study. The present invention provides an alternative where cross-linking can be triggered through addition of an oxidizing chemical, use of a natural enzyme or generation of singlet oxygen through the use of non-damaging irradiation in combination with a sensitizing molecule. As furan oxidation can be achieved through oxidation, Reactive Oxygen Species (ROS) generated in vivo at infection sites or intracellularly through oxidative stress causes target specific oxidation and cross-linking. This opens the way to site-selective medicinal applications.

The present invention provides methods for cross-linking polymers. The term "cross-linking" or "bio-conjugating" refers to linking one polymer to another with a covalent bond. The term "polymer" refers to a natural, synthetic or recombinant polymer. In the methods of the present invention, the term polymer refers preferably to a peptide.

The terms "peptide", "polypeptide" or "protein" are interchangeably used herein and relate to any natural, synthetic or recombinant molecule comprising amino acids joined together by peptide bonds between adjacent amino acid residues. A "peptide bond", "peptide link" or "amide bond" is a covalent bond formed between two amino acids when the carboxyl group of one amino acid reacts with the amino group of the other amino acid, thereby releasing a molecule of water. The peptide can be from any source, e.g. a naturally occurring peptide, a chemically synthesized peptide, a peptide produced by recombinant molecular genetic techniques or a peptide from a cell or translation system. In the context of the present invention, the peptide may be a linear chain or may be folded into a globular form. Furthermore, it is not intended that a peptide be limited by possessing or not possessing any particular biological activity.

In an embodiment, the present invention relates to methods for cross-linking peptides. The methods for cross-linking peptides comprise the steps of: a) providing a composition comprising furan-peptides, said furan-peptides comprising at least one amino acid comprising a furan-moiety; b) contacting said composition comprising furan-peptides with second peptides, thereby obtaining a mixture comprising furan-peptides and second peptides; c) adding an activation signal to said mixture of step b), thereby activating said furan-peptides to activated furan-peptides, and d) reacting said activated furan-peptides with said second peptides, thereby cross-linking said activated furan-peptides with said second peptides. The methods of the present invention are preferably performed in vitro.

The methods of the present invention thus make use of furan-peptides. The term "furan-peptide" refers to any peptide comprising a furan-moiety. The term "furan", "furyl", "furan-moiety" or "furyl-moiety" relates to a heterocyclic organic compound or functional group of Formula (Ia) or (Ib), or stereoisomeric forms thereof, consisting of five-membered aromatic ring with four carbon atoms and one oxygen atom.

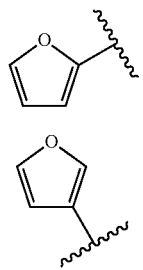

(Ia)

(Ib)

The furan-peptides of the invention comprise at least one amino acid comprising at least one furan-moiety, hereafter also referred to as furan amino acid. The furan-peptides may comprise more than 1, such as, for instance, 2, 3, 4, 5, 6, 7, 8, 9, 10, 11, 12, 13, 14, 15, 16, 17, 18, 19 or 20 furan amino acids. The furan amino acids of the invention can be located on any position in the furan-peptide, such as, for instance, N-terminally, C-terminally or internally. For instance, in case of more than one furan amino acids, a first furan amino acid may be located C-terminally and a further furan amino acid(s) may be located internally and/or N-terminally in a furan-peptide.

The furan-peptides of the invention can be obtained by any suitable method known by the person skilled in the art. In a preferred method, the furan-peptides of the present invention are obtained by incorporating at least one furan amino acid during solid-phase peptide synthesis (SPPS) of the peptide. Solid-phase peptide synthesis is a method that is widely used to chemically synthesize peptides (see, e.g., Merrifield, 1963, JACS, 85, 2149-2154) and can be adapted to produce furan-peptides. This technique typically comprises two stages: the first stage of solid phase peptide synthesis (SPPS) includes the assembly of a peptide chain using protected amino acid derivatives on a solid support via repeated cycles of coupling-deprotection. The free N-terminal amine of a solid-phase attached peptide can then be coupled to the C-terminal carboxyl of a single N-protected amino acid unit, e.g., a furan amino acid. This unit is then deprotected, revealing a new N-terminal amine to which a further amino acid may possibly be attached. While the peptide is being synthesized usually by stepwise methods, all soluble reagents can be removed from the peptide-solid support matrix by filtration and washed away at the end of each coupling step. In the second stage of SPPS, the peptide is cleaved from the support and side-chain protecting groups are removed to produce the peptide, e.g., a furan-peptide.

In an embodiment, the method for cross-linking peptides as described herein may prior to step (a) comprise producing furan-peptides by incorporating at least one furan amino acid into a peptide during solid-phase peptide synthesis (SPPS) of said peptide.

In a further embodiment, the method for cross-linking peptides as described herein may prior to step (a) comprise producing furan-peptides comprising an N-terminal furan-moiety by a method comprising the steps of:
  synthesizing peptides by coupling amino acids via amide bonds on a solid support, wherein at least the N-terminal amino acid comprises a furan-moiety, thereby obtaining furan-peptides coupled to a solid support comprising an N-terminal furan-moiety;
  capping the N-terminal amino acid of said furan-peptides comprising an N-terminal furan-moiety with a capping moiety, thereby obtaining capped furan-peptides comprising an N-terminal furan-moiety; and
  cleaving in solution said capped furan-peptides comprising an N-terminal furan-moiety from said solid support, thereby producing cleavage products in solution, wherein at least 60% of said cleavage products in solution are furan-peptides. In a preferred embodiment, said capping moiety may be an aromatic moiety.

There are two major used forms of solid phase peptide synthesis: Fmoc (Carpino et al., 1972, J. Org. Chem., 37, 3404-3409), in which a base labile alpha-amino protecting group is used, and t-Boc, in which an acid labile protecting group is used. Each method involves different solid support resins and amino acid side chain protection and consequent cleavage/deprotection steps. For additional details regarding peptide synthesis, see the following publications and references cited within: Crick et al., 1961, Nature, 192, 1227-32; Hofmann et al., 1966, JACS, 88, 5914-9; Kaiser et al., 1989, Acc. Chem. Res., 22, 47-54; Nakatsuka et al., 1987, JACS, 109, 3808-10; Schnolzer et al., 1992, Science, 5054, 221-5; Chaiken et al., 1981, CRC Crit. Rev. Biochem., 11, 255-301; Offord, 1987, Protein Eng, 1, 151-157; and Jackson et al., 1994, Science, 5183: 243-7; all of which are incorporated herein explicitly by reference.

The furan-peptides of the invention can also be obtained by incorporating at least one furan amino acid into a peptide during peptide translation in prokaryotes, such as bacteria, e.g. E. coli, in eukaryotes such as yeast or mammalian cells, enclosed as described by Young and Schultz (2010, J. Biol. Chem., 285(15), 11039-44).

In an embodiment, the method for cross-linking peptides as described herein may prior to step (a) comprise producing furan-peptides by incorporating at least one furan amino acid into a peptide during peptide translation in prokaryotes or in eukaryotes. In a further embodiment, the method for crosslinking peptides as described herein may prior to step (a) comprise producing furan-peptides by a method comprising the steps of:

providing a translation system comprising: (i) a furan amino acid, (ii) an orthogonal tRNA synthetase, or a functional fragment or variant thereof, (iii) an orthogonal tRNA, wherein said orthogonal tRNA is specifically aminoacylated by said orthogonal tRNA synthetase with the furan amino acid, and (iv) a nucleic acid encoding a peptide, wherein the nucleic acid comprises a codon that is recognized by said orthogonal tRNA; and translating the nucleic acid, thereby incorporating the furan amino acid into the peptide. In certain embodiments, said furan amino acid may be selected from a furan amino acid of Formula (XIa), (XIb) or (XIc), or a stereoisomeric form thereof, wherein X is selected from NH, O, S or P. In preferred embodiments, said furan amino acid may be selected from a furan amino acid of Formula (XIa) or (XIb) wherein X is NH or said furan amino acid may be a furan amino acid of Formula (XIc). More preferably, said furan amino acid may be selected from a furan amino acid of Formula (XIc) or (XId).

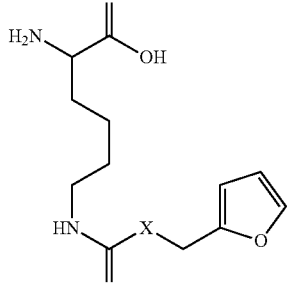

(XIa)

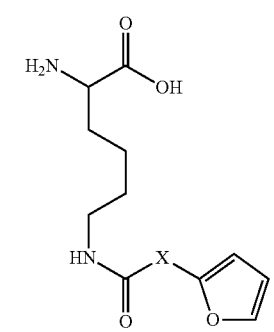

(XIb)

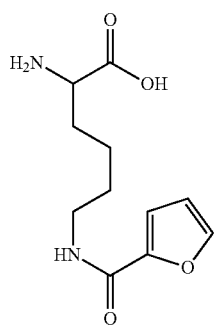

(XIc)

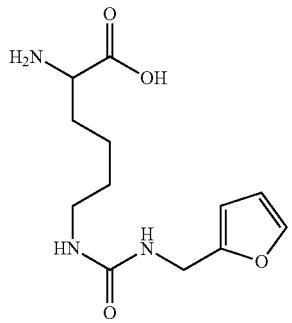

(XId)

In a preferred embodiment, the method for cross-linking peptides as described herein may prior to step (a) comprise producing furan-peptides by a method comprising the steps of:

providing a translation system comprising: (i) a furan amino acid, (ii) an orthogonal pyrrolysyl-tRNA synthetase of *Methanosarcina mazei*, or a functional fragment or variant thereof, (iii) an orthogonal tRNA-CUA of *Methanosarcina mazei*, wherein said orthogonal tRNA-CUA is specifically aminoacylated by said orthogonal pyrrolysyl-tRNA synthetase with the furan amino acid, and (iv) a nucleic acid encoding a peptide, wherein the nucleic acid comprises a codon that is recognized by said orthogonal tRNA-CUA; and translating the nucleic acid, thereby incorporating the furan amino acid into the peptide. In certain embodiments, said furan amino acid may be selected from a furan amino acid of Formula (XIa), (XIb) or (XIc), or a stereoisomeric form thereof, wherein X is selected from NH, O, S or P. In preferred embodiments, said furan amino acid may be selected from a furan amino acid of Formula (XIa) or (XIb), wherein X is NH or said furan amino acid may be a furan amino acid of Formula (XIc). More preferably, said furan amino acid may be selected from a furan amino acid of Formula (XIc) or (XId).

The furan amino acid of the present invention can be any amino acid comprising a furan moiety, for example, the furan amino acid of the present invention is selected from a furyl-glycine, furyl-alanine, furyl-valine, furyl-leucine, furyl-isoleucine, furyl-proline, furyl-tyrosine, furyl-tryptophane, furyl-phenylalanine, furyl-cysteine, furyl-methionine, furyl-serine, furyl-threonine, furyl-lysine, furyl-arginine, furyl-histidine, furyl-aspartic acid, furyl-glutamic acid, furyl-asparagine or furyl-glutamine. Preferably, the furan amino acid of the present invention may be furyl-alanine, for example furyl-L-alanine or furyl-D-alanine, more preferably furyl-L-alanine. An important advantage of furyl-alanine is that it is commercially available. Moreover, furyl-alanine can be considered as an isostere of Tyr and His. Consequently, no destabilization or alteration of the native protein structure occurs when incorporating furyl-alanine in a peptide.

The furan amino acid of the present invention may further be selected from a furan amino acid of Formula (XIa), (XIb) or (XIc), or a stereoisomeric form thereof, wherein X is selected from NH, O, S or P. Preferably, said furan amino acid may be selected from a furan amino acid of Formula (XIa) or (XIb), wherein X is NH or said furan amino acid may be a furan amino acid of Formula (XIc). More preferably, said furan amino acid may be selected from a furan amino acid of Formula (XIc) or (XId).

The furan amino acid of the present invention may further be obtained through standard organic synthesis using commercially available furan derivatives and commercially available amino acid derivatives. Commercially available furan derivatives used in the context of the present invention comprise both 2- and 3-substituted furan derivatives. For instance, commercially available furan derivatives can be selected from, but are not limited to compounds with Formula (IIa), (IIb), (IIc), (IId), (IIe), (IIf) or (IIg), or stereoisomeric forms thereof.

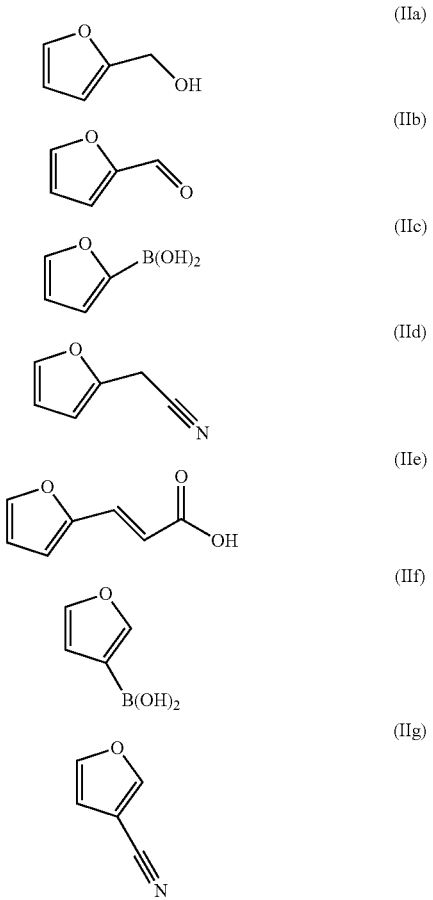

Starting from commercially available furan derivatives, other furan derivatives are within reach through standard organic synthesis known to the skilled person.

Commercially available amino acid derivatives used in the context of the present invention can for example be selected from but are not limited to compounds with Formula (IIIa) or (IIIb), or stereoisomeric forms thereof,

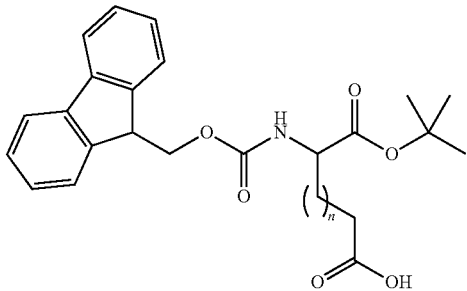

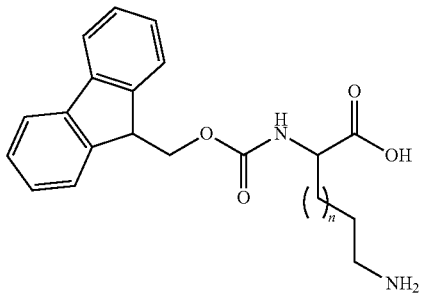

wherein n is an integer selected from 0, 1 or 2.

Figure 2:
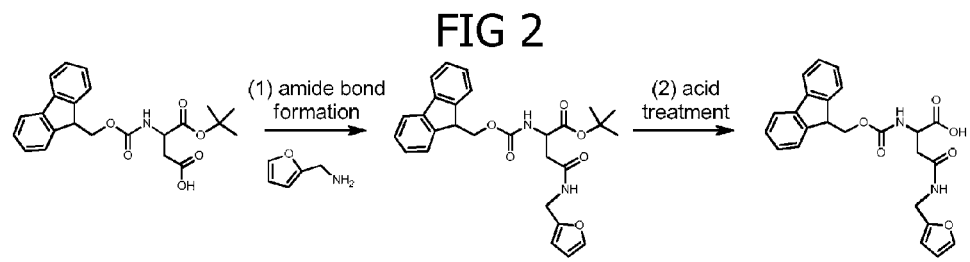
FIG. 2 schematically represents the synthesis of a furan amino acid from a commercially available furyl amine derivative and an aspartic acid derivative. (1): amide bond formation; (2): acid treatment.
Figure 3A:
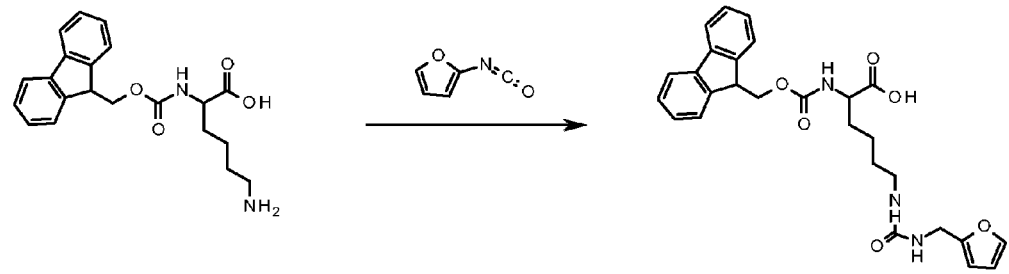
FIGS. 3A and 3B schematically represent the synthesis of a furan amino acid from a commercially available furyl isocyanate derivative or a furyl carboxylic acid derivative respectively and a lysine derivative. (1): reduction of double bond.
Figure 3B:
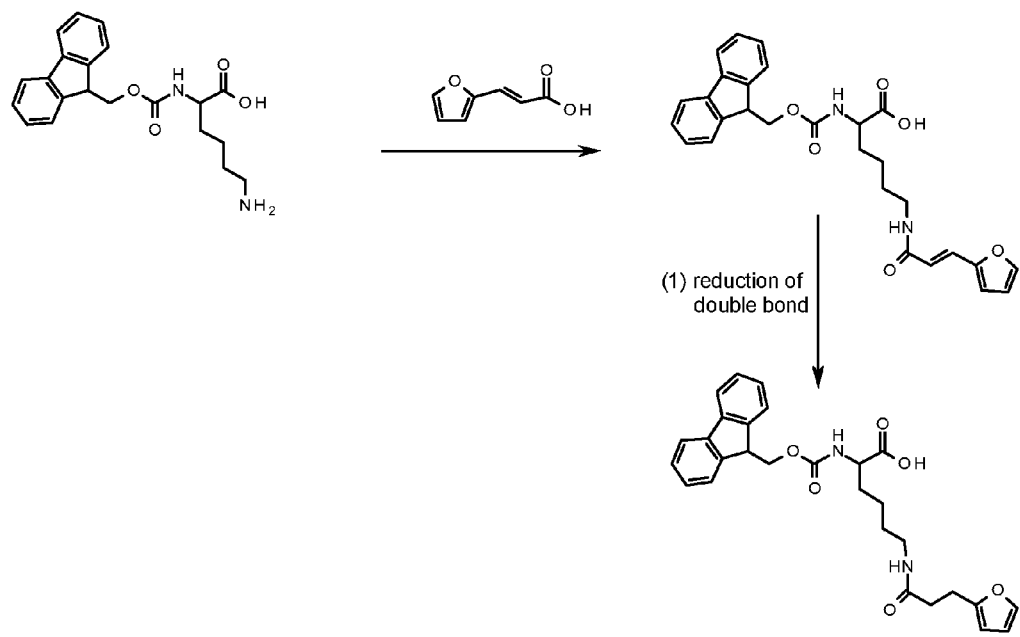

In an embodiment, the furan amino acids of the present invention are obtained through amide bond formation between a furyl amine derivative and the carboxyl group of a glutamic acid (Glu) derivative as depicted in FIG. 1. Furthermore, as shown in FIG. 2, the furan amino acids of the present invention may be obtained through amide bond formation between a furyl amine derivative and the carboxyl group of an aspartic acid (Asp) derivative. The furan amino acids of the present invention may further be obtained through amide bond formation between a furyl isocyanate derivative or a furyl carboxylic acid derivative and the amine group of Lys as shown in FIGS. 3A and 3B, respectively.

The furan amino acid used in the context of the present invention can be located in any position in the peptide. It will be understood by the skilled person, however, that sterical hindrance, e.g. of the furan amino acid, by other amino acids of the peptide should preferably be avoided. The furan amino acid of the present invention should preferably be located in a position in the furan peptide being accessible for cross-linking, e.g., the second peptide. The position of the furan amino acid of the invention in the peptide is preferably chosen based on, e.g., whether its position in a particular location would change the conformation, activity or stability of the peptide.

In an embodiment, the furan-peptides of the invention contain at least three amino acids. Preferably, the furan-peptides of the invention contain from 3 to 5000 amino acids, for example, the furan-peptides of the invention contain from 3 to 20 amino acids, for example, the furan-peptides of the invention contain 3, 4, 5, 6, 7, 8, 9, 10, 11, 12, 13, 14, 15, 16, 17, 18, 19 or 20 amino acids. Preferably, the furan-peptides of the invention contain from 20 to 50 amino acids, or from 50 to 100 amino acids, or from 100 to 1000, or from 1000 to 5000 amino acids; for example, the furan-peptides of the invention contain 20, 25, 30, 35, 40, 45, 50, 60, 70, 80, 90, 100, 200, 300, 400, 500, 600, 700, 800, 900 or 1000 amino acids or any integer in between the aforementioned values.

In embodiments, the methods of the present invention comprise the step of providing a composition comprising furan-peptides, said furan-peptides comprising at least one amino acid comprising a furan-moiety, e.g., a furan amino acid.

The composition of the invention preferably comprises furan-peptides which can be free furan-peptides or bound to a solid support. The terms "free" or "unbound" denote that the peptide is not coupled to a solid support, e.g. the furan-peptide is cleaved from the solid support on which it is synthesized. The free or unbound furan-peptides of the invention include, but are not limited to, furan-peptides in solution and dried or lyophilized peptides, such as, for instance, a powder of peptides. Because the composition of the invention can comprise free furan-peptides in solution, the composition of the invention may further comprise a solvent wherein the furan-peptides can be dissolved. Preferably, the solvent is dichloromethane (DCM), dimethylformamide (DMF), N-methyl-2-pyrrolidone (NMP) or $H_2O$, or a combination of the aforementioned solvents. In order to enhance the solubility of the free furan-peptides in solution, the composition of the invention preferably comprises trifluoroacetic acid (TFA). More preferably, the composition of the invention comprises TFA in a concentration ranging from about 0.01 to about 10%; for example, from about 0.05 to about 2.0%; for example, the composition comprises TFA in a concentration ranging from about 0.1 to about 1.0%. For example, the composition of the invention comprises TFA in a concentration of 0.05, 0.075, 0.1, 0.2, 0.3, 0.4, 0.5, 0.6, 0.7, 0.8, 0.9, 1.0, 1.5 or 2.0%, or any value in between any of the aforementioned values. The solid support of the present invention is a support on which the peptides of the invention are synthesized. The solid supports of the present invention are preferably chosen from polystyrene resins comprising an acid labile linker or polystyrene-co-polyethyleneglycol resins comprising an acid labile linker. In an embodiment, the solid support is selected from the group comprising Wang resin, Rink amide resin, ChemMatrix®, phenylacetamidomethyl (PAM) resin, Merrifield resin, and paramethyl-benzhydrylamine (pMBHA) resin. It will be understood that furan-peptides which are subsequently, e.g. after synthesizing and cleaving from the solid support, coupled, connected or linked to a further solid support, such as for instance beads, membranes, colloids, rubber or synthetic particles and the like, can be considered free furan-peptides.

The composition of the invention preferably comprises or consists of at least 60%, preferably, at least 65%, 70%, 75%, 80%, 85%, 90%, 95%, 96%, 97%, 98%, 99% or 100% of furan-peptides. The solution of the invention, or the dried, lyophilized or powder of the invention preferably comprises or consists of at least 60%, preferably, at least 65%, 70%, 75%, 80%, 85%, 90%, 95%, 96%, 97%, 98%, 99% or 100% of substantially pure furan-peptides. For example, the solution, or the dried, lyophilized or powder of the invention comprises from about 60% to about 70% of furan-peptides, for example, from about 70% to about 80% of furan-peptides, for example, from about 80% to about 90% of furan-peptides, for example, the solution, or the dried, lyophilized or powder of the invention comprises from about 90% to about 100% of furan-peptides. In an embodiment, the solution, or the dried, lyophilized or powder of the invention consists of 100% of substantially pure furan-peptides. The solution, or the dried, lyophilized or powder of the invention may further comprise undesired peptides such as dithioacetal-containing peptides or peptides containing a reduced furan-moiety such as dihydrofuranyl-containing peptides and/or tetrahydrofuranyl-containing peptides.

In embodiments, the methods of the present invention further comprise the step of exposing or contacting the composition comprising furan-peptides to second peptides, thereby obtaining a mixture between said furan-peptides and said second peptides. Preferably, the second peptide of the invention is a natural, synthetic or recombinant peptide, polypeptide or protein. The second peptides of the invention preferably comprise at least one amino acid comprising a sulfhydryl group, hydroxyl group, amine group, imidazole group or indole group. At least one amino acid of the second peptide of the invention can be cysteine, serine, threonine, tyrosine, lysine, arginine, histidine, tryptophan or any N-terminal amino acid. The second peptide of the invention may be a free second peptide or may be bound to a solid support.

The term "exposing" or "contacting" refers to bringing together the furan-peptides and the second peptides. Generally, upon exposing peptides to each other, interactions may form between said peptides. These interactions can be covalent interactions or non-covalent interactions such as electrostatic interactions, hydrogen bonds, hydrophobic interactions or van der Waals interactions. The interactions can further be transient or permanent. The site where interactions are formed between the peptides is further referred to herein as binding site. Upon exposing the furan-peptides to the second peptides, interactions may possibly be formed between the furan-peptide and the second peptide. The interactions bring the furan-peptide in close interaction with the second peptide. The distance between the furan-peptide and the second peptide upon interacting is preferably ≤20 angstrom; for example the distance between the furan-peptide and the second peptide upon interacting is ≤15 angstrom, ≤10 angstrom, ≤5 angstrom; for example, the distance between the furan-peptide and the second peptide upon interacting is 1, 2, 3, 4, 5, 6, 7, 8, 9, 10, 11, 12, 13, 14, 15, 16, 17, 18, 19 or 20 angstrom. The dissociation constant ($K_d$) of the furan-peptide and the second peptide relates to the affinity between the furan-peptide and the second peptide. Preferably, the dissociation constant of the furan-peptide and the second peptide is ≤$10^3$ μM; more preferably, the dissociation constant of the furan-peptide and the second peptide is ≤$10^2$ μM, ≤10 μM, ≤1 μM, ≤$10^2$ nM≤10 nM, ≤1 nM, ≤0.1 nM, ≤0.01 nM, ≤$10^{-3}$ nM, ≤$10^{-6}$ nM; for example, the dissociation constant of the furan-peptide and the second peptide is 100 μM, 10 μM, 1 μM, 100 nM, 10 nM, 5 nM, 1 nM, 0.5 nM, 0.1 nM, 0.05 nM, 0.01 nM, $10^{-3}$ nM, $10^{-4}$ nM, $10^{-5}$ nM or $10^{-6}$ nM; or any value in between the aforementioned values.

In further embodiments, the methods of the present invention comprise the step of adding an activation signal to the mixture of step b), thereby activating said furan-peptides to activated furan-peptides. The activation signal of the invention can be any signal that activates the furan-moiety of Formula (Ia) or (Ib), or stereoisomeric forms thereof, of a furan-peptide to an enal-moiety of Formula (IVa) or (IVb), or stereoisomeric forms thereof, as it is schematically represented below. The terms "activate" or "oxidize" relate to the oxidation of a furan-moiety to an enal-moiety. The term "enal" or "enal-moiety" or "(α,β) unsaturated aldehyde" or "reactive aldehyde" refers to an unsaturated chemical compound or reactive functional group consisting of a conjugated system of an alkene and an aldehyde. It is the reactive aldehyde-moiety that allows the formation of a covalent bond between the furan-peptide and the second peptide.

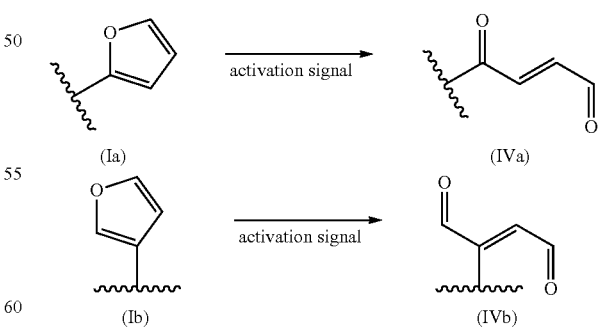

Preferably, the activation signal of the invention is selected from the group consisting of chemical oxidants, enzymes and singlet oxygen.

Chemical oxidants of the present invention are preferably selected from the group comprising or consisting of N-bromo-succinimide (NBS), NaOCl, H$_2$O$_2$ and peracids. "Peracids" or "peroxy acids" comprise acids in which an acidic —OH group has been replaced by an —OOH group. Preferably, the peracid is meta-chloroperbenzoic acid (mCPBA). Chemical oxidants as activation system have the advantage that they activate the cross-link without causing damage to the peptides to be cross-linked. As shown in Examples 3 and 5, only one equivalent of NBS was necessary to activate furan to a reactive enal. Thereby, NBS did not interfere with the binding of the second peptide to be cross-linked. Indeed, NBS caused the oxidation of the furan-moiety without degradation of the furan-peptide. It was observed that using NBS as an activation signal caused bromination of the second peptide. However, this bromination did not change the binding between the furan-peptide and the second peptide, prevented the cross-link, nor affected the analysis of the second protein.

Figure 4:
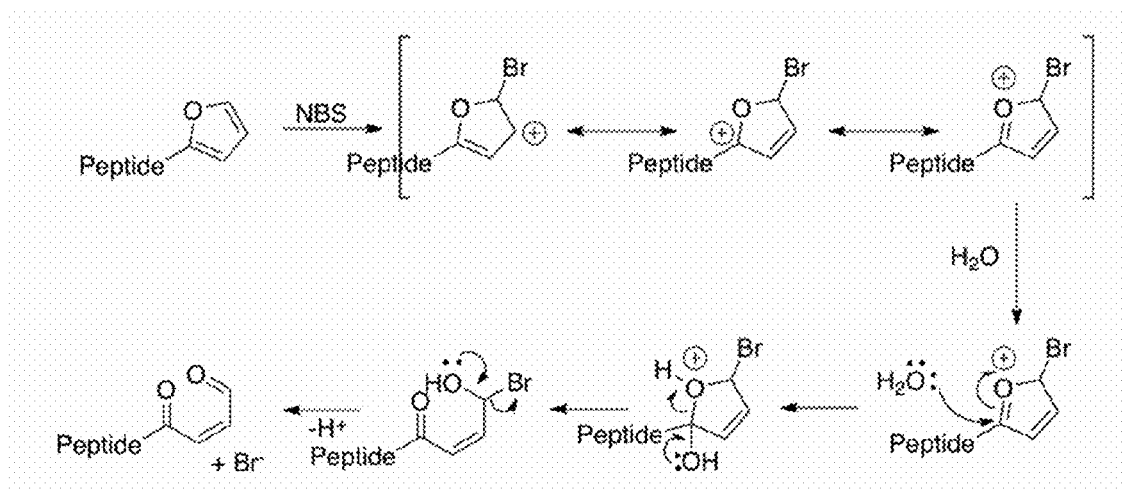
FIG. 4 schematically represents a mechanism for the activation of furan-peptides using NBS as an activation signal.

A mechanism for the selective oxidation of furan-peptides using NBS as activation signal is shown in FIG. 4. Oxidation of furan with NBS as activation signal preferably is performed in the presence of water. The mechanism includes the electrophilic addition on one of the double bonds of furan. Subsequently, water can attack on the present carbo-cation centre. After opening of the furan ring, bromide is eliminated resulting in the reactive enal-moiety.

Figure 5:
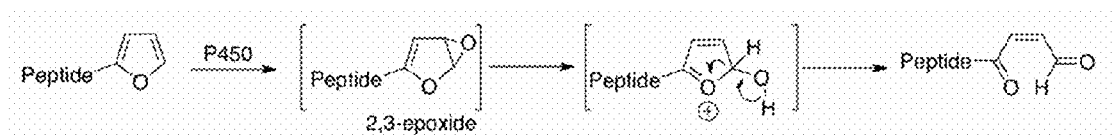
FIG. 5 schematically represents a mechanism for the activation of furan-peptides with a cytochrome P450 enzyme.

The activation signal of the invention may further be any appropriate enzyme. Preferably, said enzyme belongs to the class of cytochrome P450 enzymes. Contrary to general belief that furan-peptides should be avoided in vivo, it was found that if cross-linking of peptides is desired in vivo, an enzyme as activation signal can be advantageous because enzymes such as cytochrome P450 enzymes are present in the liver, intestines, lungs and other organs. Furthermore, an enzyme as activation signal has the advantage that it is a nondestructive activation signal, causing no damage to the peptides to be cross-linked. A mechanism for cytochrome P450 activation of the furan-peptides is given in FIG. 5. The oxidative activation of furan to a reactive (α,β) unsaturated aldehyde may be caused by the initial formation of a furan-2,3-epoxide. The opening of the furanoyl epoxide ring then leads to the formation of the reactive enal according to the invention.

The activation signal of the invention may also be singlet oxygen. Singlet oxygen is preferably generated by photoactivators in combination with sensitizers, such as, for instance, Rose Bengal or Methylene Blue. A sensitizer, such as, for example, Rose Bengal (4,5,6,7-tetrachloro-2',4',5',7'-tetraiodo-fluorescein) needs to be excited by a photo-activator such as visible light and relaxes by converting triple oxygen to singlet oxygen. Singlet oxygen as activation signal has the advantage that it is a nondestructive activation signal. Singlet oxygen is further advantageous if cross-linking of peptides is desired in humans and/or animals. The in vivo use of furan may seem counter intuitive in view of its carcinogenic properties. However, since the oxidation of furan is inducible, the formation of a reactive enal and the consequent cross-link are only triggered in the presence of an activation signal. Singlet oxygen can be specifically generated in various biological tissues by use of a sensitizer, as is demonstrated in photodynamic therapy for the treatment of tumors. In vivo activation of furan is possible because the sensitizer can be selectively absorbed by the affected cells, where it is irradiated with long wavelength light which penetrates deep into the tissue. Thereby, large amounts of reactive singlet oxygen are generated, leading to activation of the furan moiety. Studies have indicated that side reactions of singlet oxygen within a protein strongly depend on the amino acid sequence and that only Trp, the least abundant amino acid (1.13%), is sensitive to oxidation making selective oxidation of furan advantageous. The present inventors further realized that, since furan can be oxidized by peracids as described before, reactive oxygen species (ROS) released by cells during oxidative stress, for instance induced by infection, also mediate furan oxidation in vivo. Accordingly, the present invention relates to the use of furan-peptides in treating infection.

The present invention further provides free furan-peptides for use as a medicament.

Figure 6:
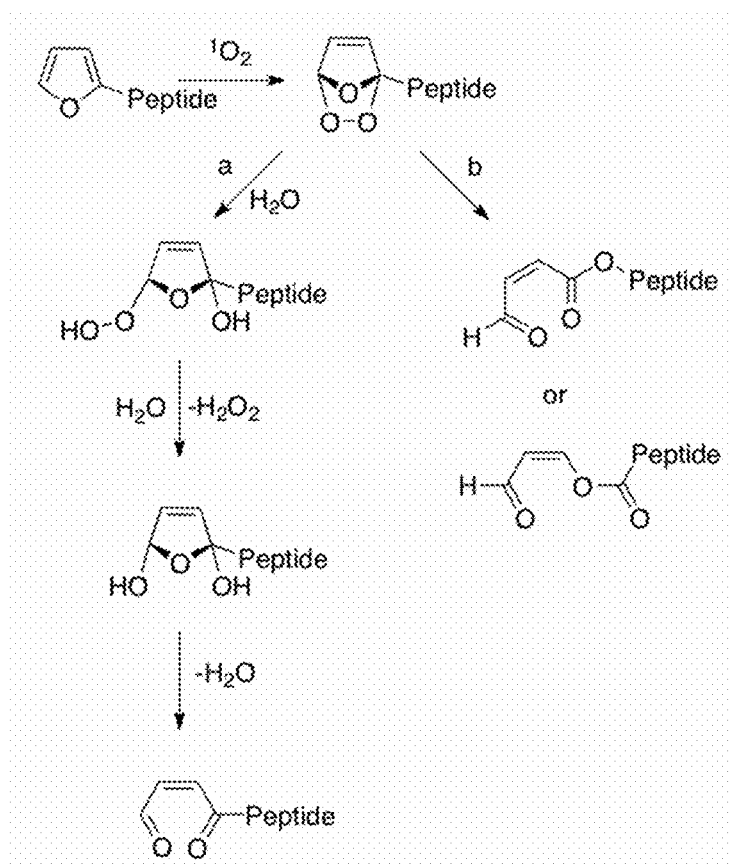
FIG. 6 schematically represents a mechanism for the activation of furan-peptides using singlet oxygen as activation signal.

A mechanism for the selective activation of furan-peptides using singlet oxygen as activation signal is shown in FIG. 6. The oxidation of furan in a furan-peptide with singlet oxygen as activation signal is performed through a [4+2] cyclo addition, wherein furan functions as diene and wherein a 2,5-endoperoxide is formed. The endoperoxide can react in different ways. By solvolysis, an unsaturated aldehyde will be formed (FIG. 6, step a). Alternatively, a Baeyer Villiger type rearrangement can result in ester derivatives, thereby also forming reactive unsaturated aldehydes (FIG. 6, route b).

Furthermore, the methods of the present invention may comprise the step of reacting the activated furan-peptides with the second peptides, thereby cross-linking said activated furan-peptides with said second peptides. In an embodiment, the activated furan-peptides of the invention comprise an enal-moiety. Preferably, the enal-moiety of the activated furan-peptides of the present invention is a (cis-2-butene-1, 4-dial)-moiety.

The enal-moiety of the activated furan-peptides of the present invention preferably reacts with a sulfhydryl group, hydroxyl group, amine group, imidazole group and/or indole group of an amino acid of the second peptide. Preferably, cross-linking occurs between said enal-moiety of said activated furan-peptides of the present invention and a sulfhydryl group of a Cys, a hydroxyl group of a Ser, Thr or Tyr, an imidazole group of a His, an indole group of a Trp, an amine group of a Lys or Arg or an alpha-amine group of the N-terminal amino acid of said second peptide.

The cross-linked products of Formula (VIa), (VIb), (VIc) or (VId), or stereoisomeric forms thereof, can be obtained after reaction of an activated furan-peptide of Formula (V) with a sulfhydryl group of a second peptide of Formula (VI).

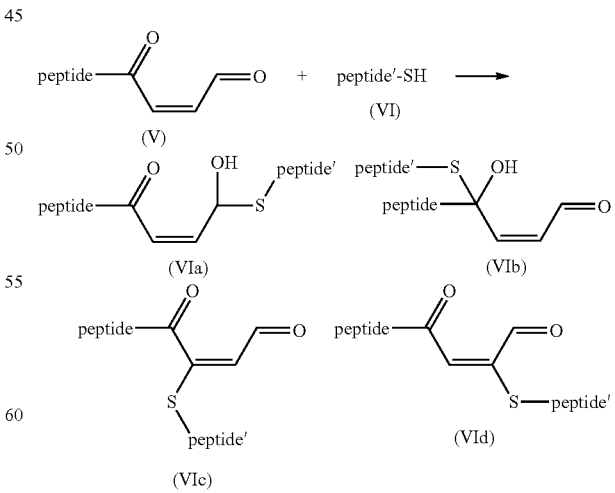

By successive reactions of a cross-linked product of Formula (VIa), (VIb), (VIc) or (VId), or stereoisomeric forms thereof, with a sulfhydryl group of a second peptide, for example peptide", cross-linked products such as, but not limited to, cross-linked products of the Formula (VIe), (VIf) or (VIg), or stereoisomeric forms thereof, can be obtained.

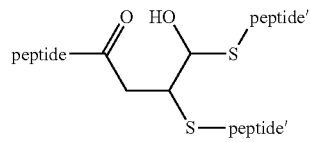
(VIe)

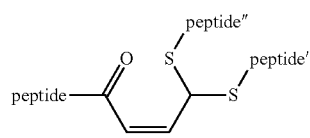
(VIf)

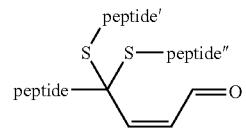
(VIg)

Upon reaction of an enal-moiety of an activated furan-peptide of Formula (V) with a hydroxyl group of a second peptide of Formula (VII), cross-linked products of Formula (VIIa), (VIIb), (VIIc) or (VIId), or stereoisomeric forms thereof, can be obtained.

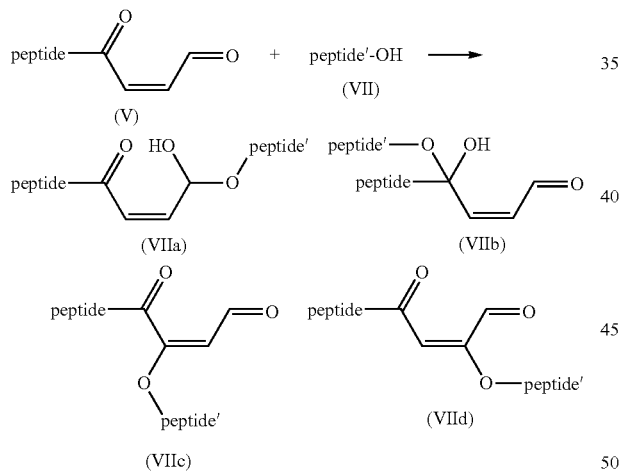

By successive reactions of a cross-linked product of Formula (VIIa), (VIIb), (VIIc) or (VIId), or stereoisomeric forms thereof, with a hydroxyl group of a second peptide, cross-linked products, such as, but not limited to, cross-linked products of the Formula (VIIe), (VIIf) or (VIIg), or stereoisomeric forms thereof, can be obtained.

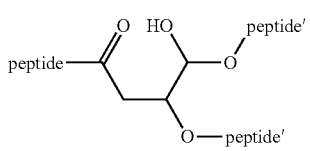
(VIIe)

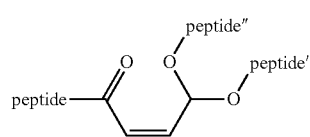
(VIIf)

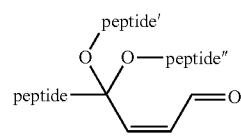
(VIIg)

Upon reaction of an enal-moiety of an activated furan-peptide of Formula (V) with an amine group of a second peptide of Formula (VIII), cross-linked products of Formula (VIIIa), (VIIIb), (VIIIc), (VIIId), (VIIIe) or (VIIIf), or stereoisomeric forms thereof, can be obtained.

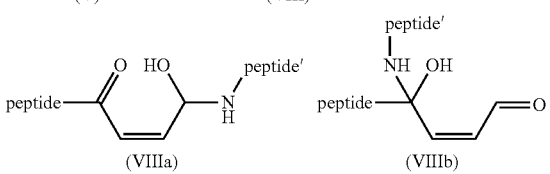

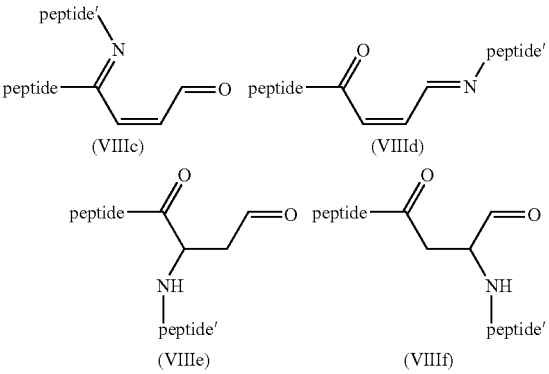

Cross-linked products such as, but not limited to, cross-linked products of Formula (VIIIg) or (VIIIh), or stereoisomeric forms thereof, can be obtained by successive reactions of, for instance, a cross-linked product of Formula (VIIIc), or stereoisomeric forms thereof, with an amine group of a second peptide.

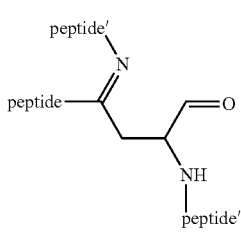
(VIIIg)

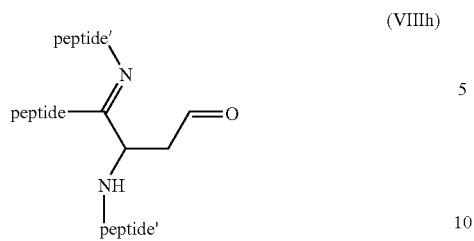

(VIIIh)

The imines of the cross-linked products of Formula (VIIIc), (VIIId), (VIIIg) or (VIIIh), or stereoisomeric forms thereof, can be transformed into more chemically stable amine derivatives. For example, the imine of the cross-linked product of Formula (VIIId), or stereoisomeric forms thereof, can be transformed into an amine derivative of Formula (VIIIk), or stereoisomeric forms thereof.

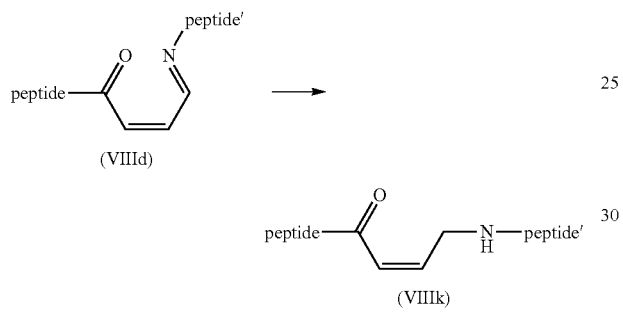

Reaction of an activated furan-peptide of Formula (V) with an imidazole group of a second peptide of Formula (IX) results in cross-linking, thereby obtaining the cross-linked products of Formula (IXa), (IXb), (IXc) or (IXd), or stereoisomeric forms thereof.

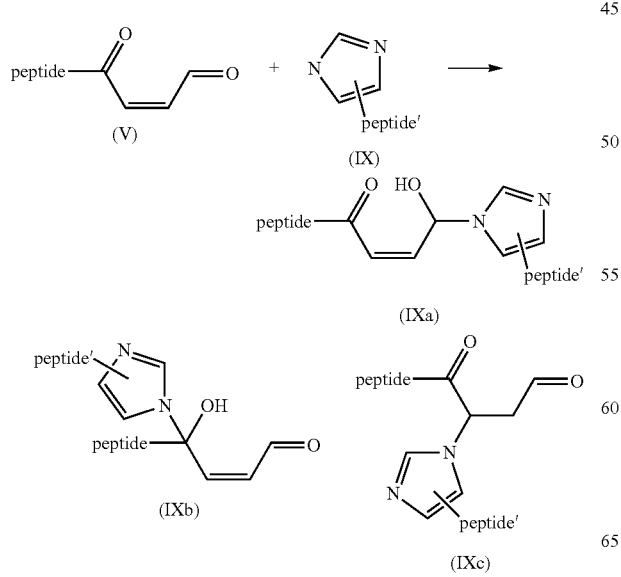

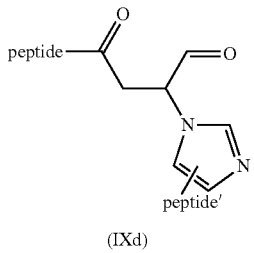

(IXd)

Upon reaction of an enal-moiety of an activated furan-peptide of Formula (V) with an indole group of a second peptide of Formula (X), the cross-linked products of Formula (Xa), (Xb), (Xc) or (Xd), or stereoisomeric forms thereof, can be obtained.

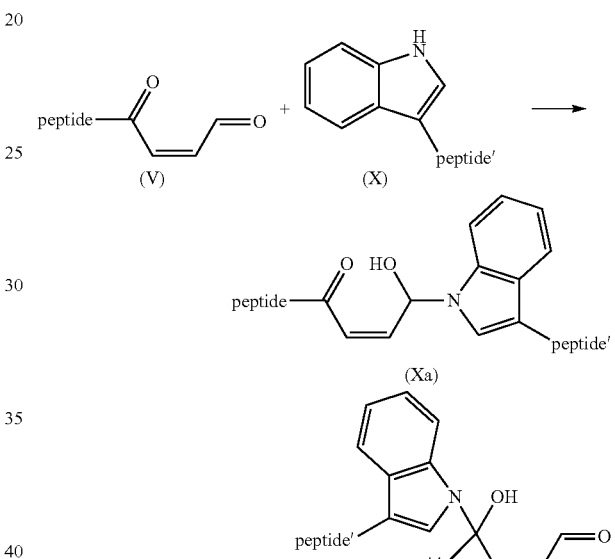

Furthermore, the cross-linked products of Formula (Xj) or (Xk), or stereoisomeric forms thereof, can be obtained after reaction of an activated furan-peptide of Formula (V) with a sulfhydryl group of a thiol of Formula (Xe) and reaction of the compounds of Formula (Xf) or (Xg) with a second peptide of Formula (Xh).

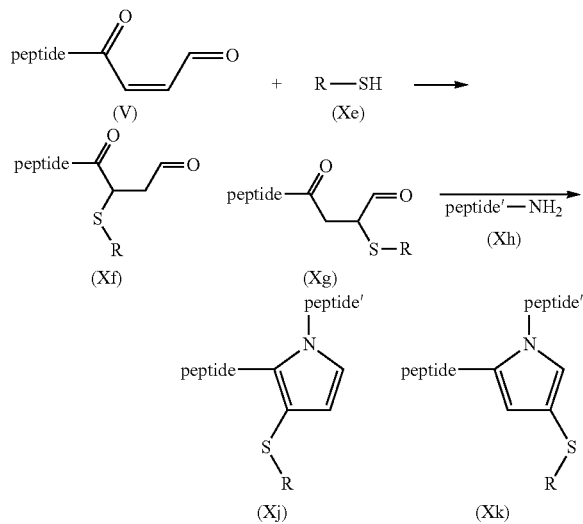

In the above-depicted Formulas of the activated furan-peptides, second peptides and cross-linked products, the peptide, peptide' and peptide" can be the same or different and are used by way of example only.

In an embodiment, the methods for cross-linking peptides comprise the steps of: a) providing a composition comprising furan-peptides, said furan-peptides comprising at least one amino acid comprising a furan-moiety; b) contacting said composition comprising furan-peptides with second peptides comprising a sulfhydryl group, hydroxyl group, amine group, imidazole group and/or indole group, thereby obtaining a mixture comprising furan-peptides and second peptides comprising a sulfhydryl group, hydroxyl group, amine group, imidazole group and/or indole group; c) adding an activation signal to said mixture of step b), thereby activating said furan-peptides to activated furan-peptides comprising an enal-moiety, and d) reacting said enal-moiety of said activated furan-peptides with said sulfhydryl group, hydroxyl group, amine group, imidazole group and/or indole group of said second peptides, thereby cross-linking said enal-moiety of said activated furan-peptides with said sulfhydryl group, hydroxyl group, amine group, imidazole group and/or indole group of said second peptides.

In embodiments, the methods of the present invention further comprise the step of identifying the cross-link between said activated furan-peptides and said second peptides. The term "cross-link" refers to a covalent bond between two polymers. In the context of the present invention, a cross-link refers preferably to a covalent bond between a peptide comprising an enal residue and a second peptide. The term "enal residue" refers to the remaining structure of the enal moiety and is formed after the reaction of the enal moiety of the activated furan-peptide with a second peptide.

Figure 7:
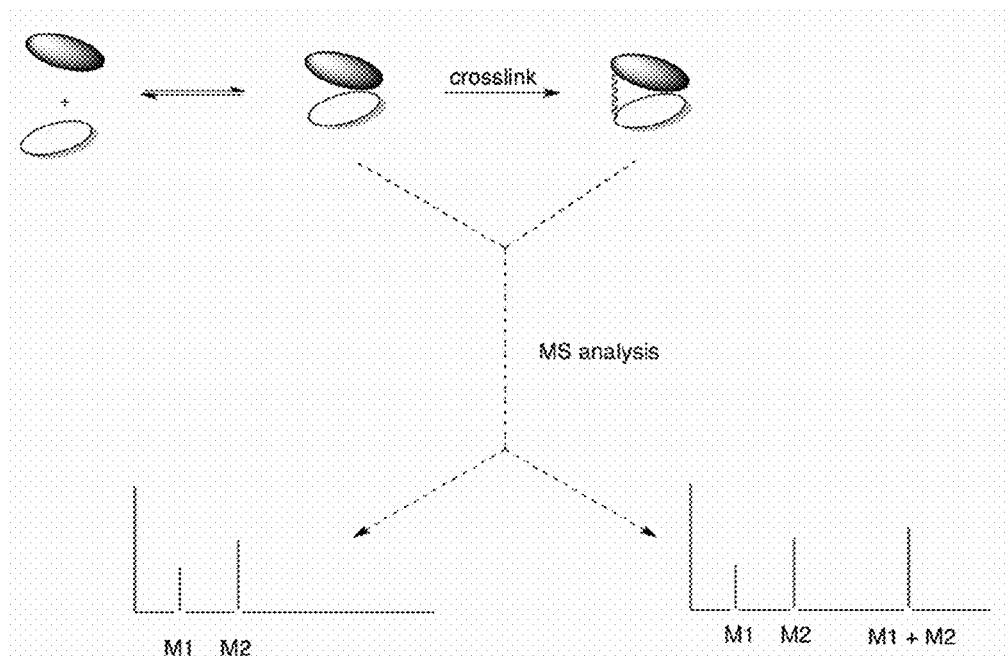
FIG. 7 schematically represents the identification of a cross-link between two peptides.

Identifying the cross-link between said activated furan-peptides and said second peptides is preferably performed by any adequate technique known to the skilled person for protein mass spectrometry (MS) analysis, preferably by gel electrophoresis, gas chromatography-mass spectrometry (GC-MS), liquid chromatography-mass spectrometry (LC-MS), high performance liquid chromatography-mass spectrometry (HPLC-MS), reversed phase high performance liquid chromatography-mass spectrometry (RP HPLC-MS), matrix-assisted laser desorption/ionization-time of flight (MALDI-TOF), electro spray ionization-mass spectrometry (ESI-MS), inductively coupled plasma-mass spectrometry (ICP-MS), accelerator mass spectrometry (AMS), thermal ionization-mass spectrometry (TI-MS) and spark source mass spectrometry (SS-MS), more preferably by gel electrophoresis, liquid chromatography-mass spectrometry (LC-MS), matrix-assisted laser desorption/ionization-time of flight (MALDI-TOF) or electro spray ionization-mass spectrometry (ESI-MS). These techniques for protein mass spectrometry analysis can optionally be preceded by a tryptic digest. Identifying the cross-link between said activated furan-peptides and said second peptides is schematically illustrated in FIG. 7.

Furthermore, the methods of the invention may comprise the step of identifying said second peptides cross-linked with said activated furan-peptides by any technique known by the skilled person for protein mass spectrometry analysis as defined above. The methods of the present invention may further comprise the step of identifying the amino acid of the second peptides reacted with the enal-moiety of the activated furan-peptide by any technique for protein mass spectrometry analysis as defined above.

The methods of the invention may be used to identify a binding site of two interacting peptides. Hence, in an embodiment, the present invention relates to the use of the methods for cross-linking peptides as described herein for identifying a binding site of two interacting peptides.

The methods of the invention may comprise further to the steps a) to d), wherein said amino acid comprising a furan-moiety is located at position n of said furan-peptides, the steps of: e) determining the cross-link of said furan-peptides and said second peptides; f) identifying said amino acid comprising a furan-moiety at position n as being a binding site of said two interacting peptides if cross-linking is detected; and g) optionally repeating steps a) to f) with said furan-peptides, wherein said amino acid comprising a furan-moiety is located at position n+p of said furan-peptides; wherein position n may be any amino acid of said furan-peptides; and wherein p is a positive or negative integer (provided position n+p is located on said furan-peptides).

In an embodiment, a method is provided for identifying a binding site of two interacting peptides comprising steps a) to d) of the method for cross-linking peptides as described herein, wherein said amino acid comprising a furan-moiety is located at position n of said furan-peptides; said method may further comprise the steps of: e) determining the cross-link of said furan-peptides and said second peptides; f) identifying said amino acid comprising a furan-moiety at position n as being a binding site of said two interacting peptides if cross-linking is detected; and g) optionally repeating steps a) to f) with said furan-peptides, wherein said amino acid comprising a furan-moiety is located at position n+p of said furan-peptides; wherein position n may be any amino acid of said furan-peptides; and wherein p is a positive or negative integer (provided position n+p is located on said furan-peptides).

In a further aspect, the present invention provides a method for identifying a binding site of two interacting peptides comprising the steps of:
a) providing a composition comprising furan-peptides, said furan-peptides comprising at least one amino acid comprising a furan-moiety, and wherein said amino acid comprising a furan-moiety is located at position n of said furan-peptides;

b) contacting said composition comprising furan-peptides with second peptides, thereby obtaining a mixture comprising furan-peptides and second peptides;
c) adding an activation signal to the mixture of step b), thereby activating said furan-peptides to activated furan-peptides;
d) reacting said activated furan-peptides with said second peptides, thereby cross-linking said activated furan-peptides with said second peptides;
e) determining the cross-link of said interacting peptides;
f) identifying said amino acid comprising a furan-moiety as a binding site of two interacting peptides if cross-linking is detected; and
g) optionally repeating steps b) to f) with said furan-peptides, wherein said amino acid comprising a furan-moiety is located at position n+1 of said furan-peptides;

wherein position n may be any amino acid of said furan-peptides; and
wherein n is a positive or negative integer (provided position n+1 is located on said furan-peptides).

In a further embodiment, a method is provided for identifying a binding site of two interacting peptides comprising the steps of:
a) providing a composition comprising furan-peptides, said furan-peptides comprising at least one amino acid comprising a furan-moiety, and wherein said amino acid comprising a furan-moiety is located at position n of said furan-peptides;
b) contacting said composition comprising furan-peptides with second peptides, thereby obtaining a mixture comprising furan-peptides and second peptides;
c) adding an activation signal to the mixture of step b), thereby activating said furan-peptides to activated furan-peptides;
d) reacting said activated furan-peptides with said second peptides, thereby cross-linking said activated furan-peptides with said second peptides;
e) determining the cross-link of said interacting peptides;
f) identifying said amino acid comprising a furan-moiety as a binding site of two interacting peptides if cross-linking is detected; and
g) optionally repeating steps a) to f) with said furan-peptides, wherein said amino acid comprising a furan-moiety is located at position n+p of said furan-peptides;

wherein position n may be any amino acid of said furan-peptides; and wherein p is a positive or negative integer (provided position n+p is located on said furan-peptides).

The present invention further relates to cross-linked products obtained or obtainable by the methods of the present invention. The terms "cross-linked peptides", "cross-linked product" or "bio-conjugate" relate to a complex of peptides comprising at least a peptide with an enal residue covalently bound to a second peptide via said enal residue.

The cross-linked peptides of the present invention can be used to study protein interactions and/or multi-protein complexes. The cross-linked peptides of the present invention are preferably used for identifying the second peptide cross-linked with the furan-peptide by any appropriate technique known in the art, such as, for instance, by protein mass spectrometry analysis as defined above. Preferably, the cross-linked peptides of the present invention are further used for identifying the amino acid of the second peptides reacted with the activated furan-peptide by any appropriate technique known in the art, such as, for instance, by protein mass spectrometry analysis as defined above.

The cross-linked peptides of the present invention are preferably also employed for therapeutic use. Because generally therapeutic peptides exhibit low stability in vivo and are often rapidly cleared, i.e. before any therapeutic effect can be achieved, frequent administration of the therapeutic peptide at high doses can be necessary to maintain activity. Such high doses can lead to undesired side effects. Furthermore, the delivery of therapeutic peptides can be restricted due to the selective permeability of membrane barriers. In embodiments, the methods of the present invention can be used for cross-linking a therapeutic peptide with a carrier peptide. The carrier peptide can promote the delivery of the therapeutic peptide into cells, can reduce the toxicity of the therapeutic peptide or can prolong its stability and/or activity following its administration to a subject. The cross-linked products of the present invention can therefore find therapeutic and/or pharmaceutical use e.g. in combination with a suitable pharmaceutical carrier.

The invention thus provides pharmaceutical compositions comprising e.g., a therapeutically effective amount of the cross-linked peptides, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering peptides are well known in the art and can be applied to administration of the cross-linked peptides of the invention.

Administration is by any of the routes normally used for introducing a molecule into ultimate contact with blood or tissue cells. The cross-linked peptides of the invention are administered in any suitable manner, optionally with one or more pharmaceutically acceptable carriers. Suitable methods of administering such cross-linked peptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Pharmaceutically acceptable carriers and excipients are well known in the art, and one or more cross-linked peptides of the invention can be formulated into pharmaceutical compositions by well-known methods (see, e.g., Remington: The Science and Practice of Pharmacy, 21st edition, A. R. Gennaro, Ed., Mack Publishing Company, 2005; Pharmaceutical Formulation Development of Peptides and Proteins, S. Frokjaer and L. Hovgaard, Eds., Taylor & Francis, 2000; and Handbook of Pharmaceutical Excipients, 3rd edition, A. Kibbe, Ed., Pharmaceutical Press, 2000).

Cross-linked peptides of the invention can be administered by a number of routes including, but not limited to: oral, intravenous, intraperitoneal, intramuscular, transdermal, subcutaneous, topical, sublingual, or rectal means. Cross-linked peptides of the invention can also be administered via liposomes. Such administration routes and appropriate formulations are generally known to those of skill in the art. The cross-linked products of the invention, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intra-articular (in the joints), intravenous, intramuscular, intra-dermal, intra-peritoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials.

Parenteral administration and intravenous administration are preferred methods of administration. In particular, the routes of administration already in use for conjugate therapeutics, along with formulations in current use, provide preferred routes of administration and formulation for the cross-linked peptides of the invention.

The dose administered to a patient, in the context of the present invention, is sufficient to effect a beneficial therapeutic response in the patient over time, or, e.g., to inhibit infection by a pathogen, to reduce or prevent the symptoms of a disease state, or other appropriate activity, depending on the application. The dose is determined by the efficacy of a particular composition/formulation, and the activity, stability or serum half-life of the carrier peptide-therapeutic peptide bioconjugate employed and the condition of the patient, as well as the body weight or surface area of the patient to be treated. The size of the dose is also determined by the existence, nature, and extent of any adverse side-effects that accompany the administration of a particular composition, or the like in a particular patient.

In determining the effective amount of the composition/formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of bio-conjugate antibodies.

The dose administered, e.g., to a 70 kilogram patient, is typically in the range equivalent to dosages of currently-used therapeutic proteins, adjusted for the altered activity or serum half-life of the relevant cross-linked peptides. The compositions/formulations of this invention can supplement treatment conditions by any known conventional therapy, including antibody administration, vaccine administration, and administration of cytotoxic agents, natural amino acid polypeptides, nucleic acids, nucleotide analogues, biologic response modifiers, and the like.

For administration, formulations of the bio-conjugates of the present invention are administered at a rate determined by the LD-50 of the relevant formulation, and/or observation of any side-effects of the cross-linked peptides at various concentrations, e.g., as applied to the mass and overall health of the patient.

Administration can be accomplished via single or divided doses. General Methods for preparing administrable compositions are known to those skilled in the art and are described in more detail in e.g., Remington: The Science and Practice of Pharmacy, 21st edition, A. R. Gennaro, Ed., Mack Publishing Company (2005).

A variety of subjects can benefit from the therapeutic treatments, and/or prophylactic treatments provided by the cross-linked peptides provided by the invention. Humans, and animals including, but not limited to, domestic livestock, such as cows, pigs, goats, sheep, chickens, and/or other common farm animals can be administered compositions and formulations that include the cross-linked peptides described herein. Common household pets, e.g., cats, dogs, parrots, parakeets, doves, etc., can also benefit from being administered therapeutic or prophylactic cross-linked peptides.

The present invention also provides free furan-peptides. Methods for incorporating furan into a peptide with solid support peptide synthesis have been described above. Subsequently, the furan-peptides should be cleaved from the solid support. Specificity and efficiency of cleavage are prime determinants for choosing cleavage conditions. Specific cleavage implies that intact peptides comprising an intact furan moiety are obtained, while circumventing unwanted side-products. The intact furan-peptides after cleavage should comprise a furan moiety which can be activated, but is not yet activated. Efficient cleavage presupposes a large yield of the required furan-peptides. Hence, the opposing requirements to cleave the synthesized furan-peptides from a solid support with high specificity on the one hand and high efficiency on the other hand, preclude standard solutions. The present inventors observed that the particulars of a specific furan-peptide, such as amino acid composition, length, position of the furan amino acid in the furan-peptide, may contribute to the efficiency and specificity of cleavage. The present inventors have developed cleavage cocktails managing these requirements appropriately, for instance, cleavage cocktails were developed, which process one or more requirements to various extents. In addition, the present inventors observed that acidic cleavage of furan-peptides comprising an N-terminal furan-moiety from a solid support with standard cleavage mixtures resulted in an unacceptable amount of undesired cleavage products. These undesired cleavage products consisted of unknown peptides, thioacetale-containing peptides or peptides containing a reduced furan-moiety such as dihydrofuranyl-containing peptides and/or tetrahydrofuranyl-containing peptides.

Therefore, the present invention further provides a method for producing furan-peptides in solution comprising the steps of: a) on a solid support, synthesizing peptides by coupling amino acids via amide bonds, wherein at least one of said amino acids comprises a furan-moiety, thereby obtaining furan-peptides coupled to a solid support, and b) cleaving in solution said furan-peptides from said solid support, thereby producing cleavage products in solution, wherein at least 60% of said cleavage products in solution are furan-peptides.

The cleavage products in solution may comprise or consist of at least 60%, preferably, at least 65%, 70%, 75%, 80%, 85%, 90%, 95%, 96%, 97%, 98%, 99% or 100% of furan-peptides. For example, the cleavage products comprise from about 60% to about 70% of furan-peptides, for example, from about 70% to about 80% of furan-peptides, for example, from about 80% to about 90% of furan-peptides, for example, the cleavage products comprise from about 90% to about 100% of furan-peptides. In a preferred embodiment, the cleavage products consist of 100% of furan-peptides substantially free of contaminants, e.g. unwanted side products. The cleavage products can further comprise dithioacetal-containing peptides or peptides containing a reduced furan-moiety such as dihydrofuranyl-containing peptides and/or tetrahydrofuranyl-containing peptides.

The furan-peptides in solution obtained by the methods of the invention may be further purified, preferably by chromatography. The furan-peptides in solution obtained by the methods of the invention may also be dried to obtain a powder, preferably by lyophilization.

In the methods of the invention, cleaving in solution of furan-peptides from said solid support is preferably performed by acidic cleavage or by basic cleavage. In the methods of the invention, cleaving in solution of furan-peptides from said solid support is preferably performed by acidic cleavage with trifluoroacetic acid (TFA) and optionally in the presence of solvents and/or scavengers. In embodiments, cleaving in solution of furan-peptides from said solid support is performed by trifluoroacetic acid (TFA) in the presence of solvents and/or scavengers. In embodiments, the solvents can be selected from the group comprising dichloromethane (DCM), dimethylformamide (DMF), N-methyl-2-pyrrolidone (NMP) and $H_2O$. In further embodiments, the scavengers can be selected from the group consisting of silane scavengers and thiol scavengers, for example the scavengers can be selected from the group comprising triisopropyl silane (TIS), 3,6-dioxa-1,8-octanedithiol (DODT), dithiothreitol (DTT), 1,2-ethanedithiol (EDT) and phenol.

Silane scavengers such as, but not limited to TIS, generally result in a higher percentage of furan-peptides in the cleavage products. However, if undesired cleavage products are obtained such as dihydrofuranyl-containing peptides and/or tetrahydrofuranyl-containing peptides, purification is complicated because these undesired cleavage products differ from the desired furan-peptides only by 2 or 4 hydrogen atoms in weight. Example 8 shows for instance that cleavage with TFA, TIS and water indeed resulted in a higher percentage of the desired furan-peptides. Thiol scavengers, such as, but not limited to, DODT, DTT or EDT, generally result in a lower percentage of desired furan-peptides in the cleavage products, as described in, for instance, Example 8. However, if undesired cleavage products such as dithioacetal-containing peptides are obtained, these unwanted cleavage products are more easily purified.

In particular embodiments, the cleavage cocktail comprising TFA, scavengers and/or solvents is selected from the group consisting of #1, #2, #3, #4, #5, #6, #7, #8, #9, #10, #11 or #12 of Table 1.

TABLE 1

Different cleavage cocktails comprising TFA, scavengers and/or solvents

| # | Cleavage cocktail | ratio |
|---|---|---|
| 1 | TFA:DCM | 1:1 |
| 2 | TFA:$H_2O$ | 95:5 |
| 3 | TFA:TIS | 95:5 |
| 4 | TFA:TIS:$H_2O$ | 95:2.5:2.5 |
| 5 | TFA:Phenol | 95:5 |
| 6 | TFA:Phenol:$H_2O$ | 95:2.5:2.5 |
| 7 | TFA:Phenol:$H_2O$:TIS | 88:5:5:2 |
| 8 | TFA:EDT | 95:5 |
| 9 | TFA:EDT:$H_2O$ | 95:2.5:2.5 |
| 10 | TFA:DTT | 95:5 |
| 11 | TFA:DTT:$H_2O$ | 95:2.5:2.5 |
| 12 | TFA:Phenol:$H_2O$:Thioanisole:EDT (Reagent K) | 82.5:5:5:5:2.5 |

In an embodiment, the present invention provides a method for producing furan-peptides comprising an N-terminal furan-moiety comprising the steps of: a) on a solid support, synthesizing peptides by coupling amino acids via amide bonds, wherein at least the N-terminal amino acid comprises a furan-moiety, thereby obtaining furan-peptides comprising an N-terminal furan-moiety coupled to a solid support, b) capping said furan-peptides comprising an N-terminal furan-moiety with a capping moiety, thereby obtaining capped furan-peptides comprising an N-terminal furan-moiety, and c) cleaving in solution said capped furan-peptides comprising an N-terminal furan-moiety from said solid support, thereby producing cleavage products in solution, wherein at least 60% of said cleavage products in solution are furan-peptides.

In a further embodiment, a method is provided for producing furan-peptides comprising an N-terminal furan-moiety comprising the steps of: a) synthesizing peptides by coupling amino acids via amide bonds on a solid support, wherein at least the N-terminal amino acid comprises a furan-moiety, thereby obtaining furan-peptides coupled to a solid support comprising an N-terminal furan-moiety; b) capping the N-terminal amino acid of said furan-peptides comprising an N-terminal furan-moiety with a capping moiety, thereby obtaining capped furan-peptides comprising an N-terminal furan-moiety; and c) cleaving in solution said capped furan-peptides comprising an N-terminal furan-moiety from said solid support, thereby producing cleavage products in solution, wherein at least 60% of said cleavage products in solution are furan-peptides.

In a particular embodiment, the present invention provides a method for producing N-terminal furan-peptides in solution comprising the steps of: a) on a solid support, synthesizing peptides by coupling amino acids via amide bonds, wherein at least the N-terminal amino acid comprises a furan-moiety, thereby obtaining N-terminal furan-peptides coupled to a solid support, b) capping said N-terminal furan-peptides with a capping moiety, thereby obtaining capped N-terminal furan-peptides, and c) cleaving in solution said capped N-terminal furan-peptides from said solid support, thereby producing cleavage products in solution, wherein at least 60% of said cleavage products in solution are N-terminal furan-peptides.

In embodiments, the N-terminal furan-peptides are furan-peptides according to the invention, wherein the furan-moiety is present in the N-terminal amino acid.

The capping moiety used in the context of the present invention is preferably an aromatic moiety. More preferably, the capping moiety of the invention is an aromatic moiety comprising at least two rings, of which at least one ring is an aromatic ring. Even more preferably, the capping moiety of the invention is selected from the group consisting of acridine-9-carboxylic acid and 2-naphtoic acid. The capping moiety of the present invention advantageously allows protection of the N-terminal furan-moiety during acidic cleavage. This unexpected stability of the N-terminal furan ring capped with an aromatic moiety can be found in $\pi$-$\pi$ stacking of the aromatic moiety with the furan ring. The capping moiety thereby protects the furan ring from degradation.

As mentioned herein, the furan-peptides of the invention can also be obtained by incorporating at least one furan amino acid into a peptide during peptide translation in prokaryotes such as bacteria, or in eukaryotes such as yeast or mammalian cells.

In an embodiment, a method is provided for producing furan-peptides comprising the step of incorporating at least one furan amino acid into a peptide during peptide translation in prokaryotes or in eukaryotes. Said method may comprise the steps of:

providing a translation system comprising: (i) a furan amino acid, (ii) an orthogonal tRNA synthetase, or a functional fragment or variant thereof, (iii) an orthogonal tRNA, wherein said orthogonal tRNA is specifically aminoacylated by said orthogonal tRNA synthetase with the furan amino acid, and (iv) a nucleic acid encoding a peptide, wherein the nucleic acid comprises a codon that is recognized by said orthogonal tRNA; and translating the nucleic acid, thereby incorporating the furan amino acid into the peptide. In certain embodiments, said furan amino acid may be selected from a furan amino acid of Formula (XIa), (XIb) or (XIc), or a stereoisomeric form thereof, wherein X is selected from NH, O, S or P. In preferred embodiments, said furan amino acid may be selected from a furan amino acid of Formula (XIa) or (XIb) wherein X is NH or said furan amino acid may be a furan amino acid of Formula (XIc). More preferably, said furan amino acid may be selected from a furan amino acid of Formula (XIc) or (XId).

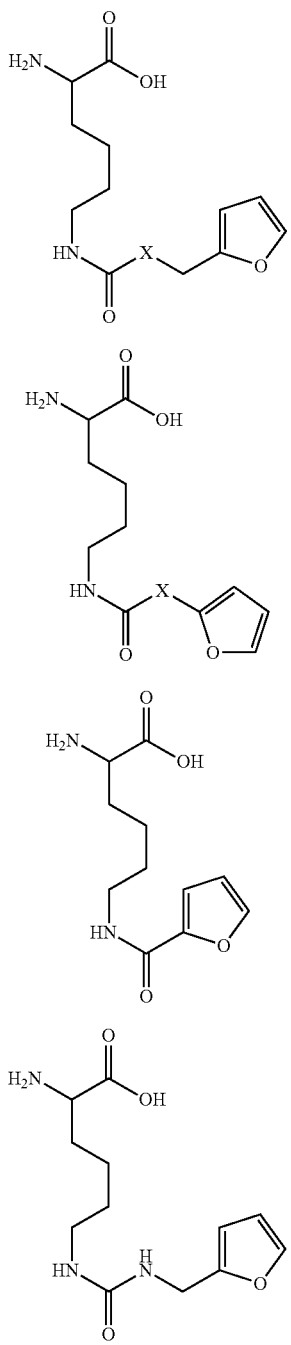

In a further embodiment, a method is provided for producing furan-peptides comprising the steps of:
  providing a translation system comprising: (i) a furan amino acid, (ii) an orthogonal pyrrolysyl-tRNA synthetase of *Methanosarcina mazei*, or a functional fragment or variant thereof, (iii) an orthogonal tRNA-CUA of *Methanosarcina mazei*, wherein said orthogonal tRNA-CUA is specifically aminoacylated by said orthogonal pyrrolysyl-tRNA synthetase with the furan amino acid, and (iv) a nucleic acid encoding a peptide, wherein the nucleic acid comprises a codon that is recognized by said orthogonal tRNA-CUA; and
  translating the nucleic acid, thereby incorporating the furan amino acid into the peptide. In certain embodiments, said furan amino acid may be selected from a furan amino acid of Formula (XIa), (XIb) or (XIc), or a stereoisomeric form thereof, wherein X is selected from NH, O, S or P. In preferred embodiments, said furan amino acid may be selected from a furan amino acid of Formula (XIa) or (XIb), wherein X is NH or said furan amino acid may be a furan amino acid of Formula (XIc). More preferably, said furan amino acid may be selected from a furan amino acid of Formula (XIc) or (XId).

The present invention also relates to free furan-peptides obtainable by any of the methods described above. The present invention further relates to free N-terminal furan-peptides obtainable by any of the methods described above.

In a further aspect, the present invention relates to a kit comprising furan-peptides comprising at least one amino acid comprising a furan-moiety and components or instructions for cross-linking said furan-peptides with second peptides according to the methods of the present invention. In embodiments, the kits comprise furan-peptides comprising at least one amino acid comprising a furan-moiety and instructions for cross-linking said furan-peptides with second peptides according to the methods of the present invention. In further embodiments, the kits according to the present invention further comprise an activation signal for activating the cross-link between furan-peptides and second peptides. In further embodiments, the kits according to the present invention further comprise second peptides for cross-linking with said furan-peptides. In particular embodiments, the kits according to the present invention comprise instructions for cross-linking said furan-peptides with second peptides according to the methods of the present invention.

Amino acids with their three letter code and one letter code are listed in Table 2.

TABLE 2

Amino acids with their three letter code and one letter code

| Amino acid | Three letter code | One letter code |
|---|---|---|
| glycine | Gly | G |
| alanine | Ala | A |
| valine | Val | V |
| leucine | Leu | L |
| isoleucine | Ile | I |
| proline | Pro | P |
| tyrosine | Tyr | Y |
| tryptophan | Trp | W |
| phenylalanine | Phe | F |
| cysteine | Cys | C |
| methionine | Met | M |
| serine | Ser | S |
| threonine | Thr | T |
| lysine | Lys | K |
| arginine | Arg | R |
| histidine | His | H |
| aspartic acid | Asp | D |
| glutamic acid | Glu | E |
| asparagine | Asn | N |
| glutamine | Gln | Q |

EXAMPLES

Example 1

Synthesis of Furan-StrepTagII Peptides in Solution

In order to show the cross-link between peptides, an in vitro model system based on the interaction between the StrepTagII and streptavidin was used. The first available Strep-Tag (AWRHPQFGG; SEQ ID NO: 19) able to bind streptavidin could only be attached to the C-terminus of a protein. By changing the sequence of the Strep-Tag, a StrepTagII was developed that can be both N-terminally and C-terminally modified without losing its affinity for streptavidin. Because the intermolecular interactions between the StrepTagII and streptavidin are well characterized, StrepTagII-streptavidin is an excellent model for testing cross-linking. Furthermore, biotin binds streptavidin on the same binding site as the StrepTagII and with a much higher affinity. Biotin will therefore specifically inhibit the StrepTagII-streptavidin interaction.

A first objective was the synthesis of free furan-peptides in solution and furan-peptides bound to a solid support in order to test if cross-linking of peptides could be performed both with furan-peptides in solution and with solid-phase bound furan-peptides.

Figure 8:
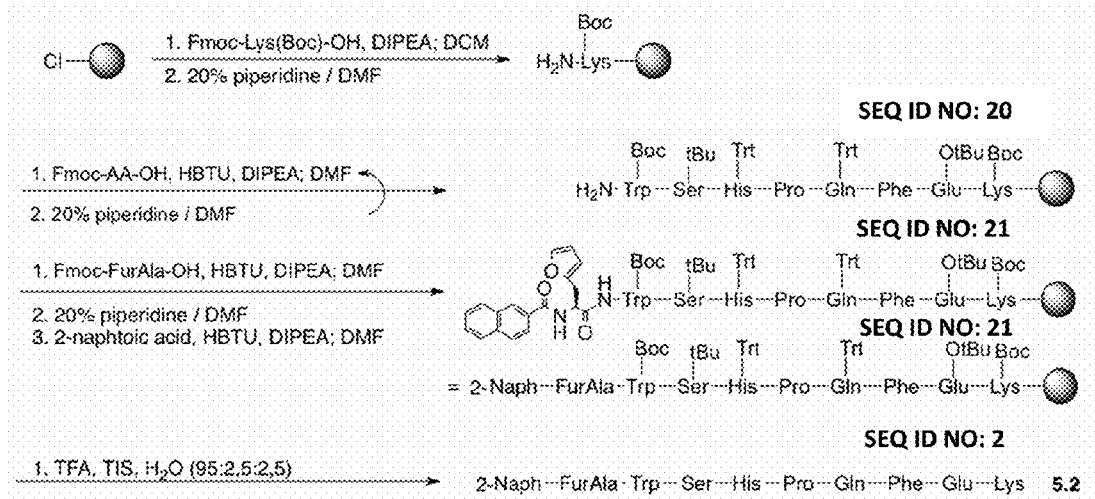
FIG. 8 schematically represents the synthesis of a free N-terminal 2-naphtoyl-furan-StrepTagll.

First of all, N-terminal furan-StrepTagII peptides in solution were synthesized. Synthesis of a StrepTagII with N-terminal (2-furyl)-alanine was performed with solid-phase peptide synthesis on a 2-chlorotrityl chloride resin as shown in FIG. 8. The first amino acid, Fmoc-lysine, was manually coupled. After deprotection of Fmoc with piperidine in DMF, the synthesis of the StrepTagII continued automatically. Fmoc-(2-furyl)-alanine was subsequently coupled to the StrepTagII followed by Fmoc deprotection with piperidine in DMF and capping with 2-naphtoic acid. Subsequently, the N-terminal furan-StrepTagII was cleaved with a cleavage cocktail comprising TFA, TIS and water (95:2.5:2.5). Cleavage products were obtained comprising substantially pure N-terminal furan-StrepTagII peptides 5.2 capped with 2-naphtoic acid. Indeed, a composition was obtained comprising substantially pure N-terminal furan-peptides in solution. The degradation of the furan moiety during acidic cleavage was avoided by using a capping moiety.

Figure 9:
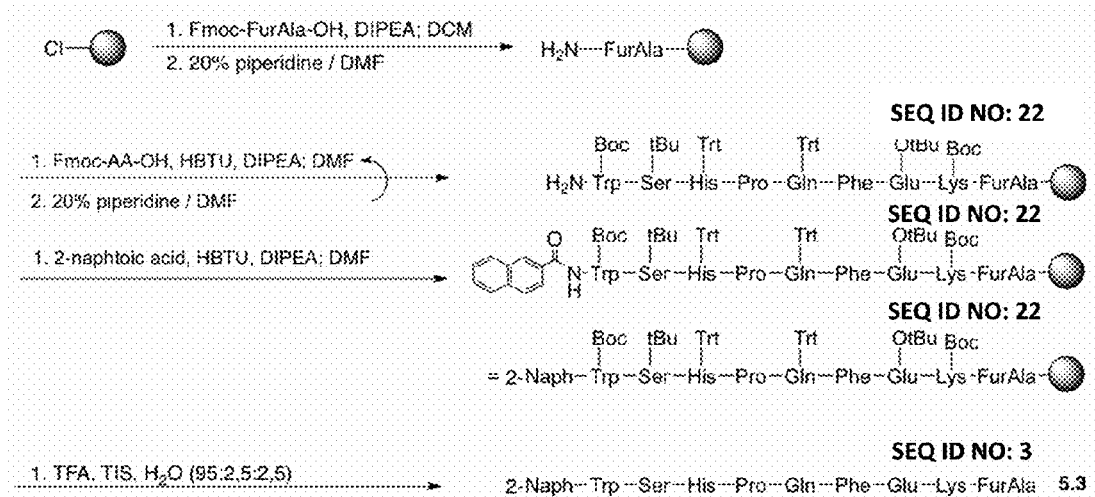
FIG. 9 schematically represents the synthesis of a free C-terminal furan-StrepTagll, N-terminally naphtoylated.

Secondly, in order to test the influence of the position of the furan amino acid in the furan-peptide on cross-linking, free furan-StrepTagII peptides were synthesized in which the furan amino acid was C-terminally incorporated. Synthesis of a StrepTagII with C-terminal (2-furyl)-alanine was performed on 2-chlorotrityl chloride resin as shown in FIG. 9. The first amino acid, Fmoc-(2-furyl)-alanine, was manually coupled. After deprotection of Fmoc with piperidine in DMF, the synthesis of the StrepTagII continued automatically. The C-terminal furan-StrepTagII was N-terminally capped with 2-naphtoic acid. Because 2-naphtoic acid has a specific absorbance in the UV-VIS spectrum, its incorporation in the StrepTagII could ease the identification of labeled streptavidin. Subsequently, the C-terminal furan-StrepTagII was cleaved with a cleavage cocktail comprising TFA, TIS and water (95:2.5:2.5). Cleavage products comprising substantially pure C-terminal furan-StrepTagII peptides 5.3 were obtained. Indeed, C-terminal modification of the peptide with a furan-moiety was obtained using Fmoc-(2-furyl)-alanine.

Example 2

Synthesis of Solid-Phase Bound Furan-Strep-TagII Peptides

In an aspect, furan-peptides bound to a solid support were synthesized.

Figure 10:
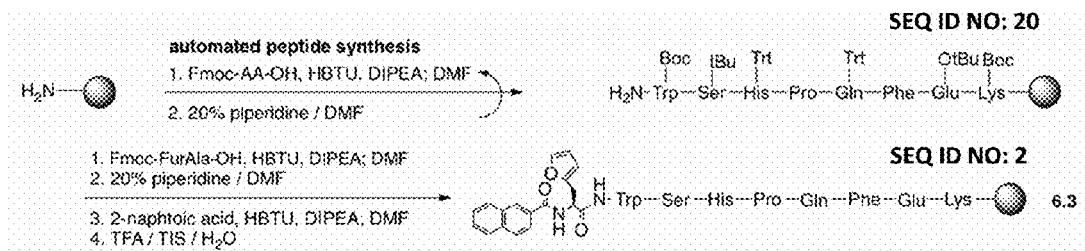
FIG. 10 schematically represents the synthesis of an N-terminal 2-naphtoyl-furan-StrepTagll on a solid support.

Synthesis of a StrepTagII with N-terminal (2-furyl)-alanine capped with 2-naphtoic acid was performed with SPPS on a ChemMatrix® solid support as shown in FIG. 10. The ChemMatrix® solid support may be an Aminomethyl-ChemMatrix®. The amino acids of the StrepTagII were automatically coupled. Fmoc-(2-furyl)-alanine was subsequently coupled to the StrepTagII followed by Fmoc deprotection with piperidine in DMF and capping with 2-naphtoic acid. Deprotection of the amino acid side chains was performed by shaking for 1 h in a mixture of TFA, TIS and water. As a result, the solid-phase bound, N-terminal furan-StrepTagII peptide 6.3 was obtained.

Figure 11:
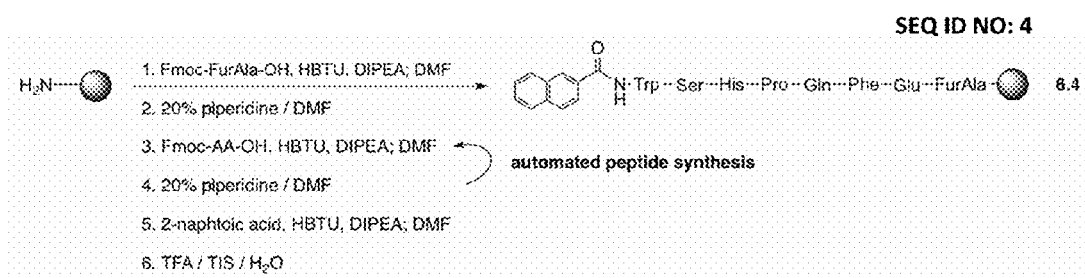
FIG. 11 schematically represents the synthesis of a C-terminal furan-StrepTagll, N-terminally naphtoylated, on a solid support.
Figure 12:
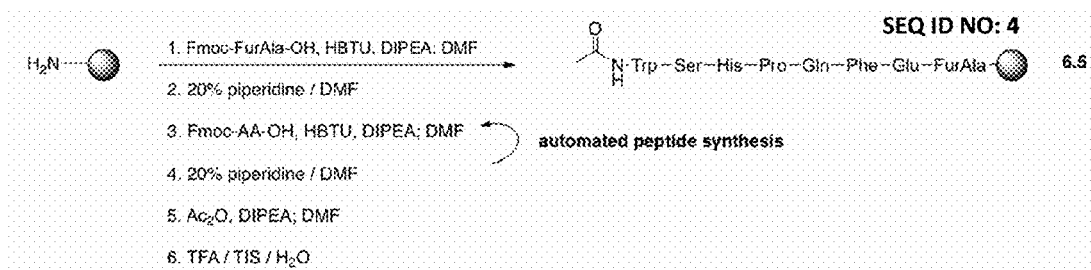
FIG. 12 schematically represents the synthesis of a C-terminal furan-StrepTagll, N-terminally acetylated, on a solid support.

Synthesis of a 2-naphtoic acid-StrepTagII with C-terminal (2-furyl)-alanine was performed with SPPS on a ChemMatrix® solid support as shown in FIG. 11. Synthesis of an acetyl-StrepTagII with C-terminal (2-furyl)-alanine was similarly performed as shown in FIG. 12. The C-terminal furan amino acid, Fmoc-(2-furyl)-alanine, was manually coupled to the resin. After deprotection of Fmoc with piperidine in DMF, the synthesis continued automatically. The StrepTagII was N-terminally protected with 2-naphtoic acid (FIG. 11) or acetic acid anhydride (FIG. 12) followed by deprotection of the amino acid side chains by shaking for 1 h in a mixture of TFA, TIS and water. The solid-phase bound C-terminal furan-StrepTagII peptides 6.4 and 6.5 were respectively obtained.

The methods of the present invention allow efficient synthesis of substantially pure furan-peptides both in solution and bound to a solid support.

Example 3

Oxidizing a Furan-StrepTagII to an Activated Furan-StrepTagII with N-Bromosuccinimide (NBS)

Figure 13:
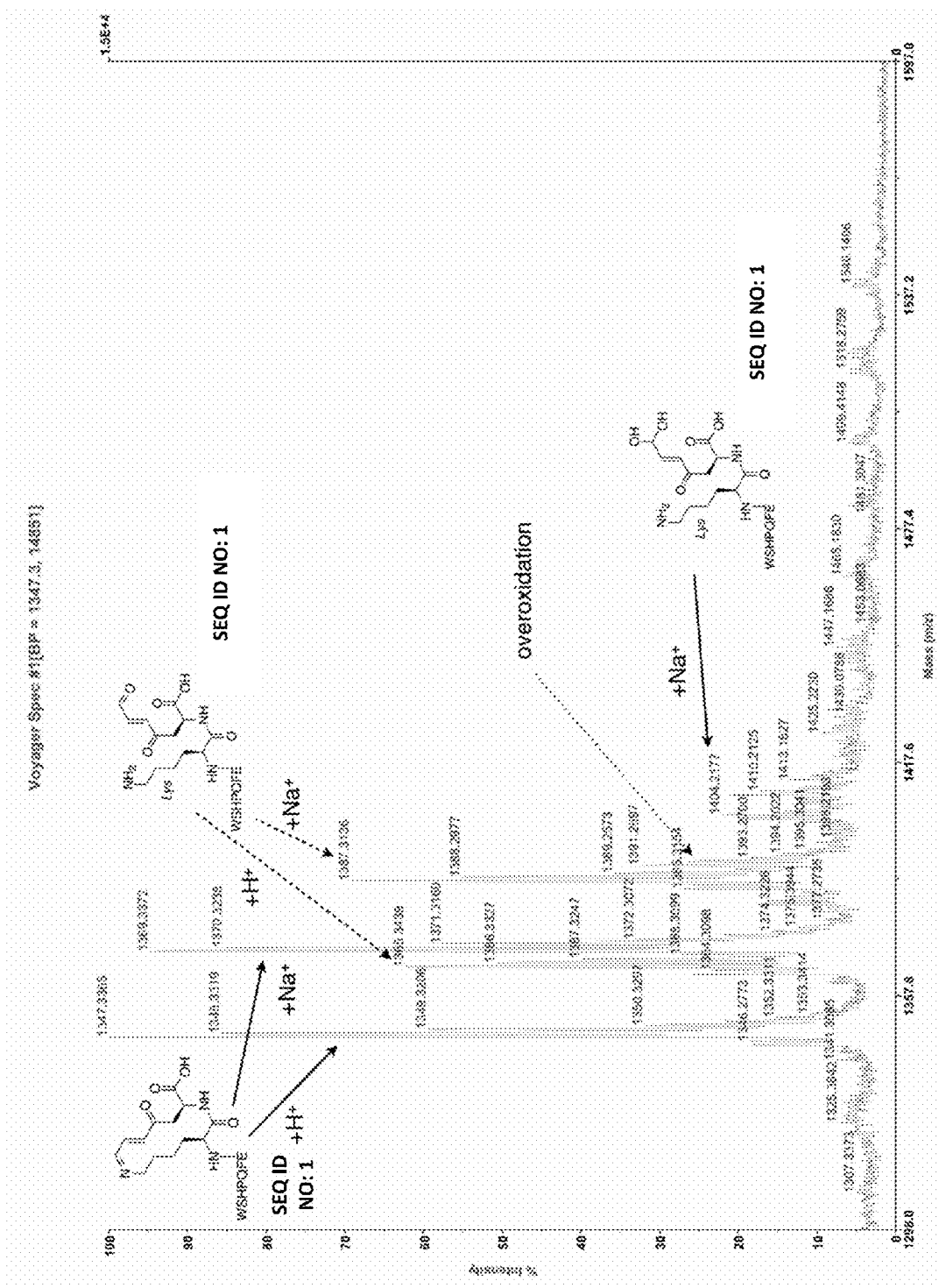
FIG. 13 represents a MALDI-TOF spectrum after the activation of a free C-terminal furan-Strep-Tagll with N-bromosuccinimide.

Different activating agents were tested for their ability to activate the furan-peptides. In first instance, N-bromosuccinimide (NBS) was tested as activating agent. NBS was added as an activation signal to free C-terminal furan-StrepTagII peptides 5.3, synthesized as described in Example 1. One equivalent of NBS was sufficient to selectively oxidize the furan-moiety of 5.3 to a reactive enal-moiety in phosphate buffered saline (PBS). As shown in FIG. 13, a major amount of the activated free C-terminal furan-StrepTagII had the desired molecular weight reduced with the molecular weight of water. This reduction in molecular weight could be due to intramolecular imine bonds which could form between the opened furan-moiety and the neighboring Lys amino acid. Also a minimal amount of over-oxidation was observed, probably due to oxidation of the indole ring in Trp. Unexpectedly and advantageously, one equivalent of NBS was sufficient to selectively activate the furan-moiety into a reactive enal-moiety.

Therefore, NBS was sufficient in low amounts to selectively and completely oxidize the furan-moiety without degradation of the furan-peptides, and further enabling analysis.

Further chemical oxidants in low amounts give substantially the same results, e.g. selectively and completely oxidize the furan-moiety without degradation of the furan-peptides, and further enabling analysis.

Example 4

Figure 14:
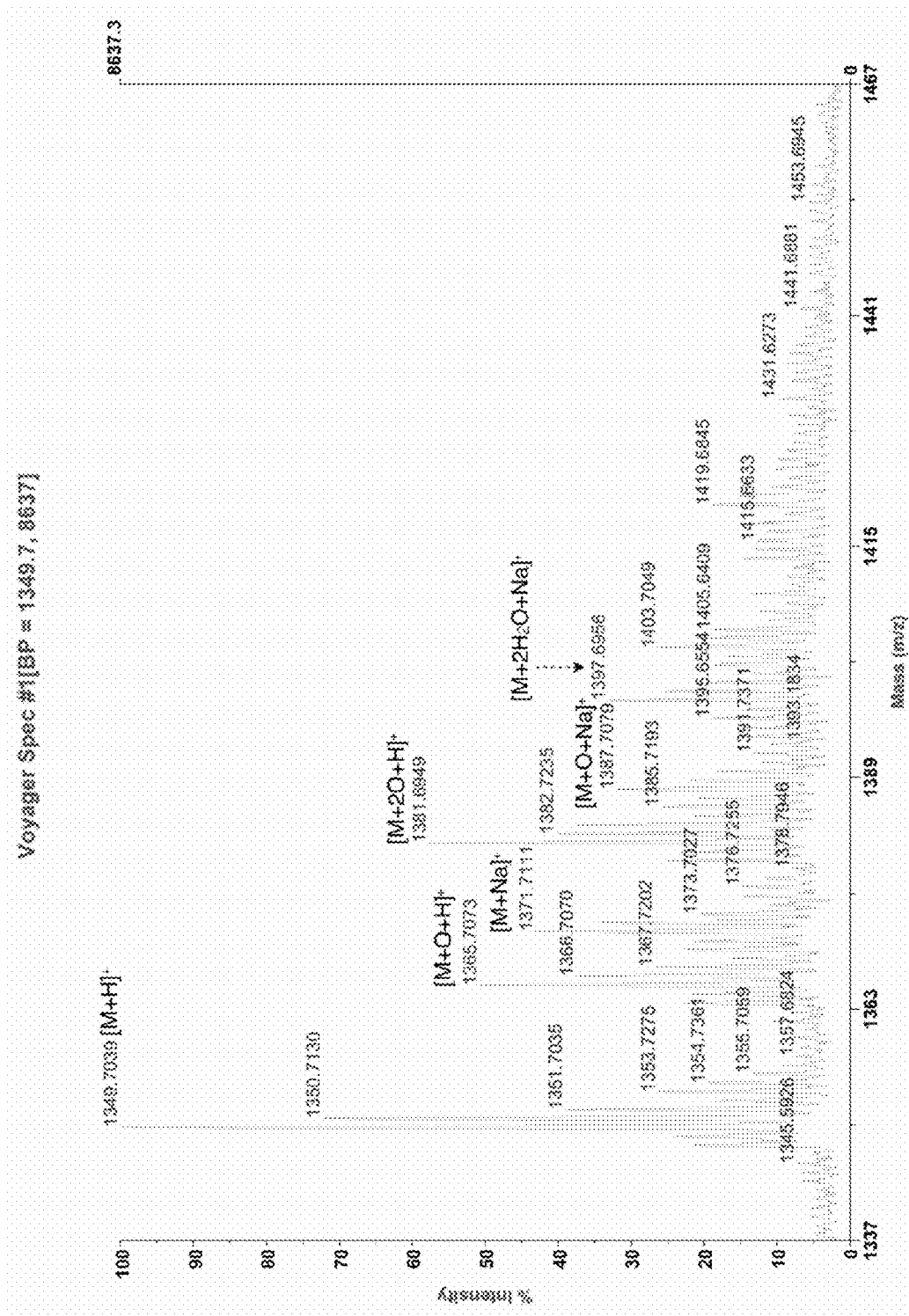
FIG. 14 represents a MALDI-TOF spectrum after the activation of a free C-terminal furan-Strep-TagII with singlet oxygen.

Activating a Furan-StrepTagII to an Activated Furan-StrepTagII with Singlet Oxygen In a further aspect, singlet oxygen was tested for its ability to activate a furan-moiety of a furan-peptide to a reactive enal. The sensitizer Rose Bengal (4,5,6,7-tetrachloro-2',4',5',7'-tetraiodo-fluorescein) was added at a concentration of 0.2 µM to the C-terminal furan-StrepTagII peptides 5.3, synthesized as described in Example 1. The mixture was radiated during 1 hour with visible light. As shown in FIG. 14, a mixture of the start product, aldehyde and over-oxidation products was obtained.

Singlet oxygen was thus able to activate the furan-moiety to a reactive aldehyde.

Further optimizing wave length and/or radiation duration results in a larger amount of activated furan-peptides and less side products.

Example 5

Cross-Linking Free Furan-StrepTagII Peptides with Streptavidin

The free N-terminal and C-terminal furan-StrepTagII peptides 5.2 and 5.3, obtained as described in Example 1, were used to test cross-linking with streptavidin using the furan-oxidation method.

Figure 15:
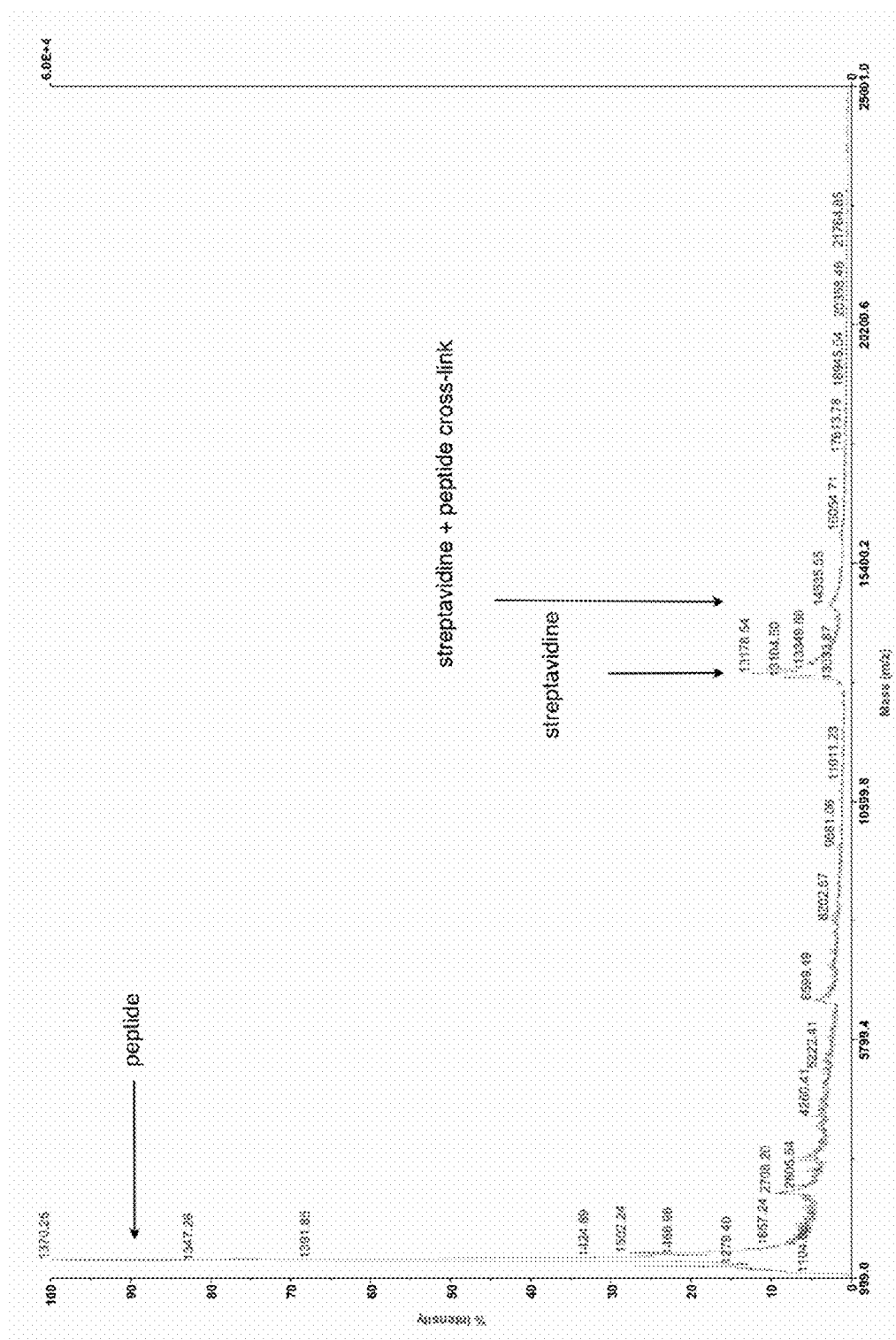
FIG. 15 represents a MALDI-TOF spectrum after cross-linking a free C-terminal furan-StrepTagII with streptavidin.

Ten equivalents of the furan-peptides 5.2 or 5.3 were mixed with streptavidin and incubated during 60 min at 37° C. One equivalent of NBS per equivalent of peptide was added as an activation signal and the reaction mixture was incubated during 2 hours at 10° C. with shaking. Optionally formed imines were selectively reduced with $NaCNBH_3$. Peptide cross-linking was observed both for the N-terminal furan-StrepTagII peptide 5.2 with streptavidin and for the C-terminal furan-StrepTagII peptide 5.3 with streptavidin (as shown in FIG. 15). The cross-link between the N-terminal furan-StrepTagII peptide 5.2 and streptavidin was less explicit than the cross-link between the C-terminal furan-StrepTagII peptide 5.3 and streptavidin. This is however not unexpected since the N-terminus of the furan-StrepTagII peptide 5.2 is located outside of its binding site with streptavidin.

These results show that NBS activated the furyl-moiety of the furan-StrepTagII peptides without interfering with the binding of streptavidin. Furthermore, bromination of streptavidin was observed during the cross-link experiment; however, it did not alter the binding of the StrepTagII.

A cross-link was thus shown between a furan-peptide and a second peptide. Furthermore, the cross-link between the furan-peptide and the second peptide occurred independently of the position of the furan-moiety in the furan-peptide. NBS was able to activate the furan-moiety for cross-linking without degradation of the furan-peptide and did not change the binding between the furan-peptide and the second peptide.

Example 5a

Identification of the Binding Site of Cross-Linked Peptides

The binding site of two interacting peptides or proteins, i.e., the site of cross-linking of a furan-peptide and a second peptide, is determined by performing an enzymatic or chemical digest of the cross-linked product. Standard conditions include trypsine or alpha-chymotrypsin digest or CNBr protein cleavage. Proteome analysis techniques such as LC-MS/MS and MALDI TOF/TOF is used to analyze the fragments of the peptides or proteins and provide detailed information on the location of the cross-link site as well as the chemical nature of the cross-link through sequencing of the cross-linked peptide fragment. In addition to the analysis of the proteome, an enrichment of the cross-linked peptide fragment using an affinity tag, such as the biotine-avidin system, can provide a reduction of background and simplify the identification of cross-linked fragments in complex mixtures. The use of isotope coded affinity tags (ICATs) also aids in identification of cross-linked peptide fragments by unambiguously indicating relevant masses as double peaks in mass spectra.

Example 6

Specific Inhibition of the Cross-Link of Free Furan-StrepTagII Peptides with Streptavidin In order to test the specificity of the StrepTagII-streptavidin cross-link, the experiment of Example 5 was repeated in the presence of biotin. As mentioned before, biotin binds streptavidin with high affinity and on the same binding site as the StrepTagII and can therefore act as a specific inhibitor of the cross-link.

Figure 16:
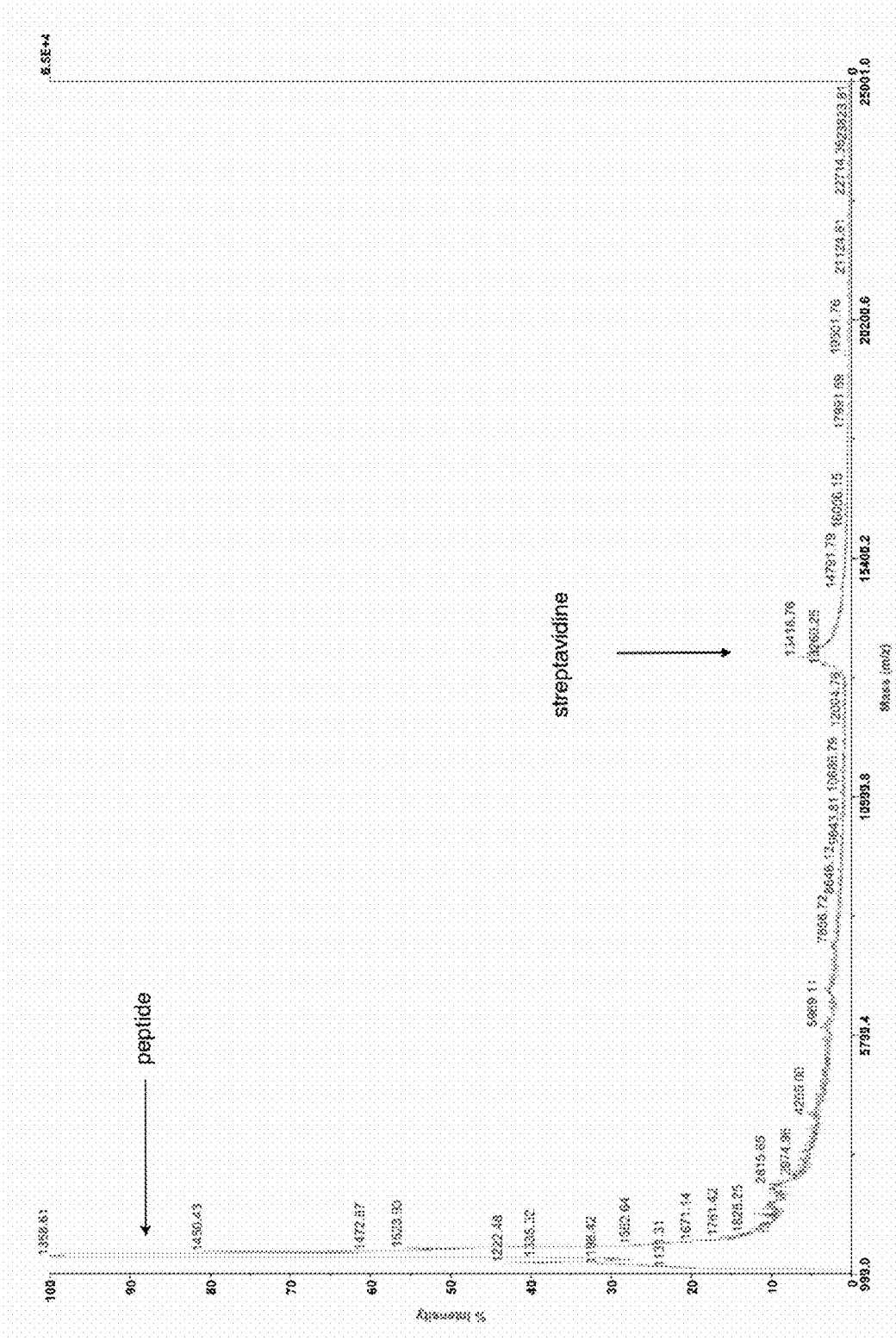
FIG. 16 represents a MALDI-TOF spectrum after cross-linking a free C-terminal furan-StrepTagII with streptavidin in the presence of biotin.

Ten equivalents of the furan-StrepTagII peptides 5.2 or 5.3, obtained as described in Example 1, were mixed with streptavidin and biotin and incubated during 60 min at 37° C. One equivalent of NBS per equivalent of peptide was added and the reaction was performed during 2 hours at 10° C. with shaking. Optionally formed imines were selectively reduced with $NaCNBH_3$. As shown in FIG. 16, no cross-link between the C-terminal furan-Strep-TagII 5.3 and streptavidin was observed in the presence of biotin, indicating that the cross-link between the C-terminal furan-StrepTagII and streptavidin is specific. Similar results were obtained with the N-terminal furan-StrepTagII peptide 5.2.

These results thus show that cross-linking with the furan-oxidation method occurred specifically between interacting furan-peptides and second peptides.

Example 7

Cross-Linking Solid-Phase Bound Furan-StrepTagII Peptides with Streptavidin

In order to test cross-linking of solid-phase bound furan-peptides using the furan-oxidation method, the solid-phase bound N-terminal furan-Strep-TagII peptide 6.3 and the C-terminal furan-Strep-TagII peptides 6.4 and 6.5 were synthesized as described in Example 2. The cross-link between the solid-phase bound furan-peptides and streptavidin-HRP was studied. HRP is an enzyme that converts $H_2O_2$ to $H_2O$ in the presence of an electron donor. The substrate 4-chloro-naphtol will be used as electron donor and causes a dark purple color after oxidation. Since the enzymatic reaction is catalyzed, even a minimal amount of enzyme bound to the solid support will result in a detectable signal.

Figure 17A:
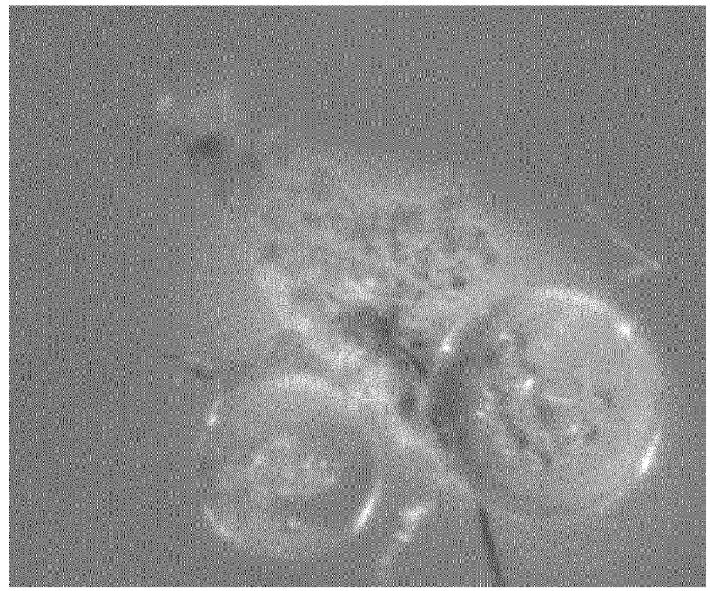
FIG. 17 represents images illustrating the cross-link between solid-phase bound furan-StrepTagII and streptavidin.
Figure 17B:
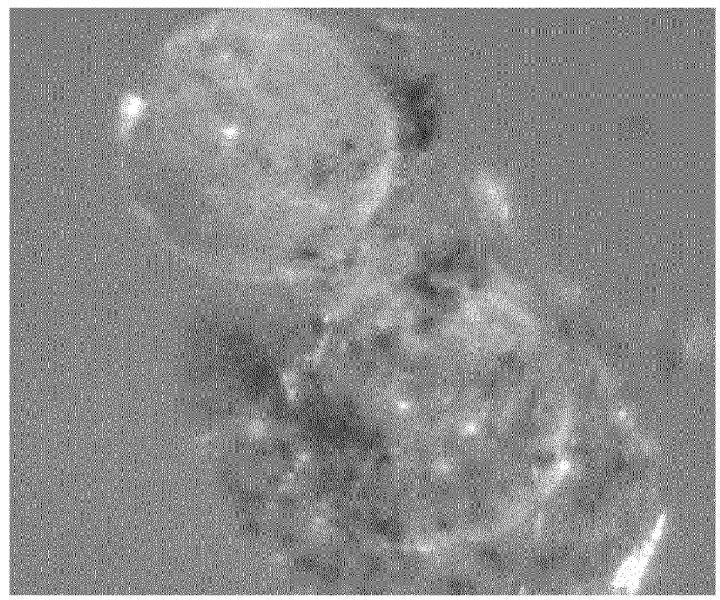
Figure 17C:
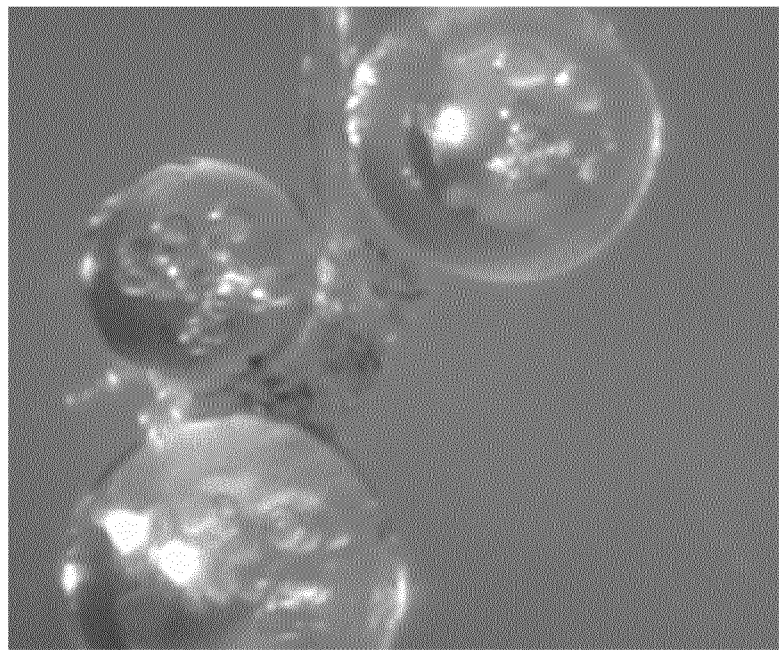

The furan-peptides 6.3, 6.4 and 6.5 were synthesized on a ChemMatrix® solid support which has a low affinity for peptides, thereby avoiding non-specific binding of the furan-peptides on the solid support. Solid-phase bound N-terminal furan-StrepTagII peptide 6.3 and solid-phase bound C-terminal furan-StrepTagII peptides 6.4 and 6.5 were washed subsequently with dichloromethane (5 times), dimethylformamide/water (7:3, 5:5; 3:7, each 5 times) and water (5 times). To assure blocking of non-specific binding places on the solid support, the solid-phase bound furan-peptides 6.3, 6.4 or 6.5 were treated with a solution comprising 2% BSA, 0.1% Tween-20 and PBS at pH 7.4. Next, the solid-phase bound furan-peptides 6.3, 6.4 or 6.5 were washed 5 times with 0.1% Tween-20 in PBS followed by overnight incubation with 1 U/ml of streptavidin-horse radish peroxidase (HRP) in a solution of 2% BSA and 0.1% Tween-20 in PBS. Subsequently, in order to activate the furan-moiety, one equivalent of NBS per peptide was added. After 30 min, the reaction solution was removed by filtration and one equivalent of $NaCNBH_3$ in PBS was added for the selective reduction of imines. After 30 min of incubation, wash steps with dichloromethane (5 times), dimethylformamide/water (7:3, 5:5; 3:7, each 5 times) and water (5 times) were performed. The chromogen substrate 4-chloro-naphtol was added together with $H_2O_2$. As shown in FIG. 17, a dark colored resin was observed for each of the solid-phase bound furan-peptides 6.3 (FIG. 17A), 6.4 (FIG. 17B) and 6.5 (FIG. 17C), indicating cross-linking of solid-phase bound furan-StrepTagII with streptavidin-HRP. The dark purple color observed for the solid-phase bound furan-peptides shows that nor NBS nor $NaCNBH_3$ disrupt the activity of HRP. Furthermore, the example illustrates that the observed bromination of streptavidin caused by NBS does not alter the activity of streptavidin.

Comparative Example 1

Cleavage of N-Terminal Furan-Peptides with a Standard Cleavage Cocktail Comprising TFA, DTT and Water Introduction of a furan moiety as a reactive enal functionality in furan-peptides allows cross-linking of the furan-peptide with a second peptide. However, major difficulties are experienced when trying to obtain furan-containing peptides in solution and attempting to translate the furan-oxidation technology towards solution conditions. The main problems occur during the acidic cleavage of the peptide. Therefore, an objective was to obtain substantially pure furan-peptides in solution.

Figure 18:
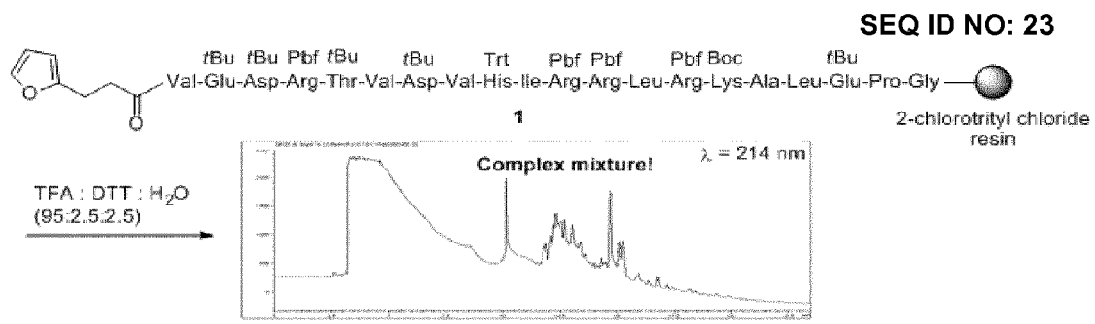
FIG. 18 represents a HPLC analysis after the cleavage of an N-terminal furan-peptide with TFA, DTT and water.

As shown in FIG. 18, an N-terminal furan-peptide 1 was synthesized by SPPS on a 2-chlorotrityl chloride resin by introducing a furan moiety through N-terminal capping with 3-(2-furyl)-propanoic acid. The furan-peptide 1 was cleaved using a standard cleavage cocktail comprising TFA, DTT and water (95:2.5:2.5). Cleavage of 1 yielded a very complex mixture of cleavage products as evidenced by RP-HPLC. Furthermore, LC-MS analysis showed that none of the mass signals could be correlated to the expected products.

Therefore, cleavage of N-terminal furan-peptides from a solid support using a standard cleavage cocktail resulted in a complex mixture of unknown cleavage products.

Comparative Example 2

Cleavage of N-Terminal Furan-Peptides with TFA, TIS and Water

For optimization of the cleavage step, a furan-peptide was prepared and DTT was no longer used as a scavenger, but was replaced by TIS.

Figure 19:
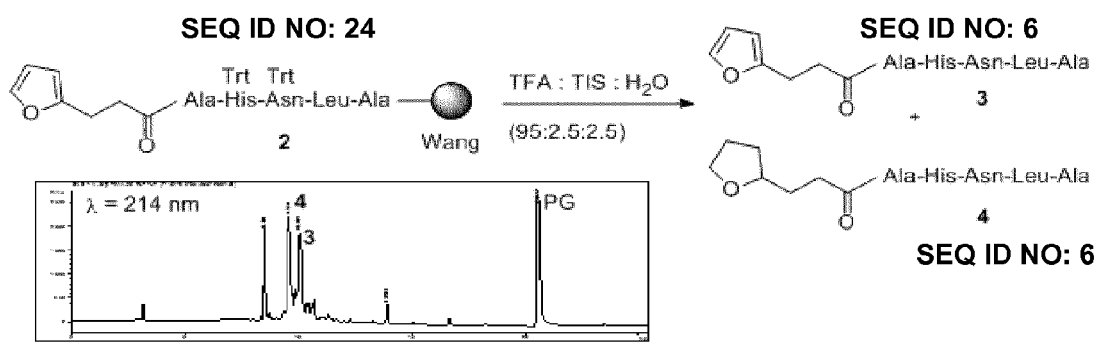
FIG. 19 represents a HPLC analysis after the cleavage of an N-terminal furan-peptide with TFA, TIS and water.

As shown in FIG. 19, a 5-mer N-terminal furan-peptide 2 was synthesized on a Wang resin by N-terminally introducing (2-furyl)-alanine. The furan-peptide 2 was cleaved using a cleavage cocktail comprising TFA, TIS and water (95:2.5: 2.5). Cleavage of 2 resulted in cleavage products comprising the desired furan-peptide 3 and reduced tetrahydrofuranyl-peptide 4.

Therefore, cleavage from a solid support of N-terminal furan-peptides using a cleavage cocktail comprising TFA, TIS and water (95:2.5:2.5), results in cleavage products comprising furan-peptides and undesired cleavage products.

Example 8

Cleavage of Internal Furan-Peptides with TFA and Scavengers

It was hypothesized that the specificity and efficiency of cleaving furan-peptides from a solid support might be dependent on the cleaving cocktail. A furan-peptide comprising an internal furan amino acid was tested using different cleaving cocktails.

Figure 20:
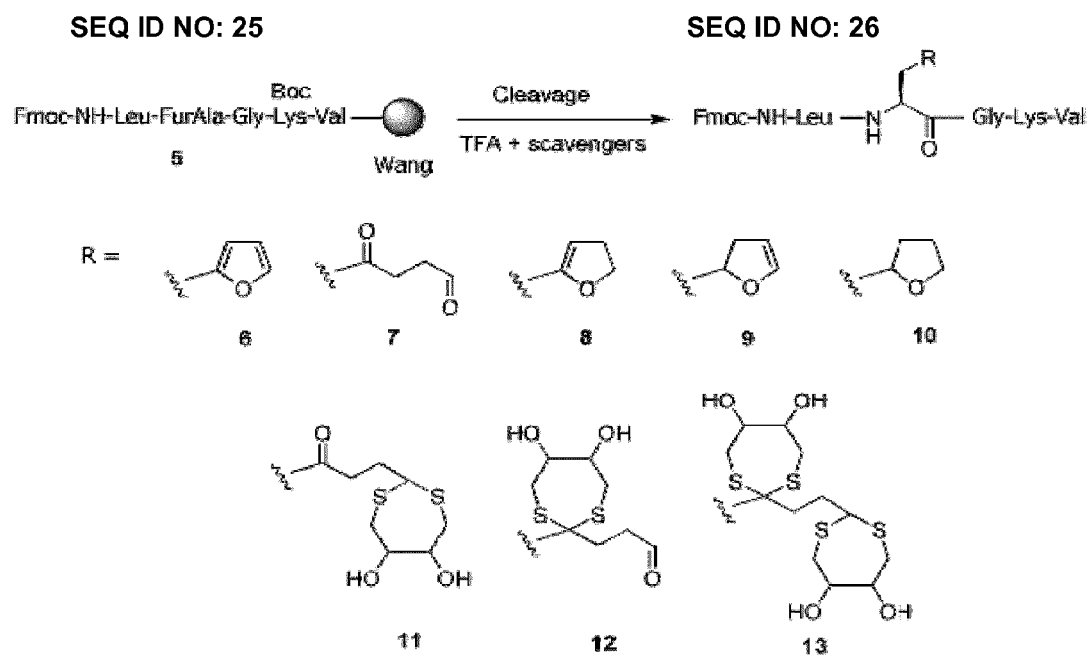
FIG. 20 illustrates the cleavage products obtainable after cleavage of an internal furan-peptide with several cleavage cocktails.

As shown in FIG. 20, a 5-mer internal furan-peptide 5 was synthesized on a Wang resin by internally introducing (2-furyl)-alanine during SPPS. The furan-peptide 5 was cleaved using different cleavage cocktails. When using a cleavage cocktail comprising TFA, TIS and water (95:2.5:2.5), the furan moiety was partially hydrogenated (7, 8, 9 and/or 10). However, a higher percentage of the desired furan-peptide was obtained. When using a cleavage cocktail comprising TFA, DTT and water (95:2.5:2.5), a lower percentage of the desired furan-peptide was obtained and unwanted dithioacetal-containing peptides were formed (11, 12 and/or 13). Advantageously, these dithioacetal-containing peptides are easily purified from the furan-peptides. The highest yields of the desired furan-peptide 6 were obtained using TIS or DTT as scavengers. Therefore, further experiments were performed using a cleavage cocktail comprising TFA, TIS and water (95:2.5:2.5).

Table 3 shows the cleavage products obtained after cleavage with different cleavage cocktails.

TABLE 3

Different cleavage products formed after cleavage with different cleavage cocktails

| # | Cleavage cocktail | Ratio | Products |
|---|---|---|---|
| 1 | TFA:DCM | 1:1 | 6 |
| 2 | TFA:H₂O | 95:5 | 6 (50%) + 7 |
| 3 | TFA:TIS | 95:5 | 6 (65%) + 8 + 9 + 10 |
| 4 | TFA:TIS:H₂O | 95:2.5:2.5 | 6 (55%) + 7 + 8 + 9 + 10 |
| 5 | TFA:Phenol | 95:5 | 6 (60%) + unidentified |
| 6 | TFA:Phenol:H₂O | 95:2.5:2.5 | 6 (30%) + 7 + unidentified |
| 7 | TFA:Phenol:H₂O:TIS | 88:5:5:2 | 6 (45%) + 8 + 9 + 10 |
| 8 | TFA:EDT | 95:5 | 6 (25%) + unidentified |
| 9 | TFA:EDT:H₂O | 95:2.5:2.5 | 6 (25%) + unidentified |
| 10 | TFA:DTT | 95:5 | 6 (40%) + 11 + 12 + 13 |
| 11 | TFA:DTT:H₂O | 95:2.5:2.5 | 6 (80%) + 11 or 12 |

Example 9

Cleavage of C-Terminal and Internal Furan-Peptides with TFA, TIS and Water (95:2.5:2.5)

A series of furan-peptides were designed, in which the position of the furylalanine residue was varied in order to determine the influence of the furan position within the furan-peptide on the reaction outcome.

Figure 21:
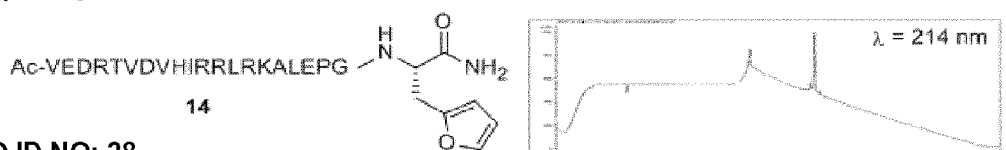
FIG. 21 represents HPLC analysis after the cleavage of a C-terminal furan-peptide and after the cleavage of internal furan-peptides with TFA, TIS and water.
Figure 21:
Figure 21:
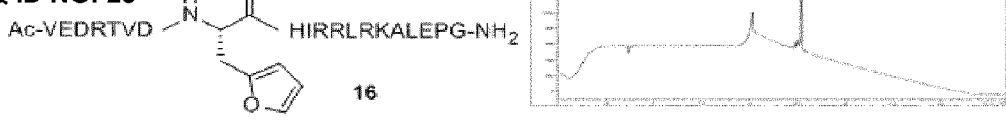
Figure 21:
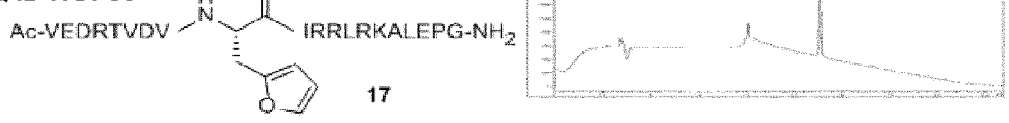
Figure 21:
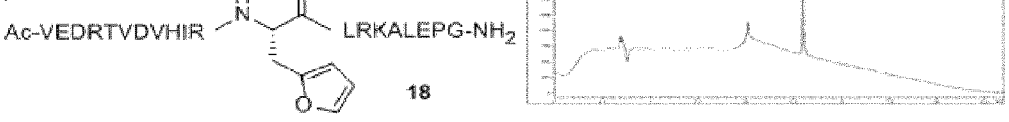

As shown in FIG. 21, cleavage of a 20-mer C-terminal furan-peptide 14 synthesized on a Rink amide resin was performed with a cleavage cocktail comprising TFA, TIS and water (95:2.5:2.5). The furan moiety was found to be completely stable during the acidic cleavage with TFA, TIS and water. Pure furan-peptides were obtained, suggesting that the furan-moiety was protected by the resin against hydrogenation during cleavage.

As further shown in FIG. 21, cleavage of 20-mer internal furan-peptides 15, 16, 17 and 18 synthesized on a Rink amide resin was performed with a cleavage cocktail comprising TFA, TIS and water (95:2.5:2.5). For all furan-peptides 15, 16, 17 and 18, pure products were obtained corresponding to the desired free furan-peptides. No hydrogenation of the furan ring was observed.

Therefore, C-terminal and internal furan-peptides in solution were obtained after SPPS using Fmoc-(2-furyl)-alanine and acidolytic cleavage with TFA, TIS and water.

Example 10

Cleavage of Capped N-Terminal Furan-Peptides with TFA, TIS and Water (95:2.5:2.5)

If N-terminal furan was introduced as Fmoc-(2-furyl)-alanine and the N-terminal furan-peptide cleaved with TFA, TIS and water, complete degradation could be observed upon cleavage from the solid support. Surprisingly, the stability of the N-terminal furan was enhanced by capping the N-terminus with a capping moiety.

Figure 22:
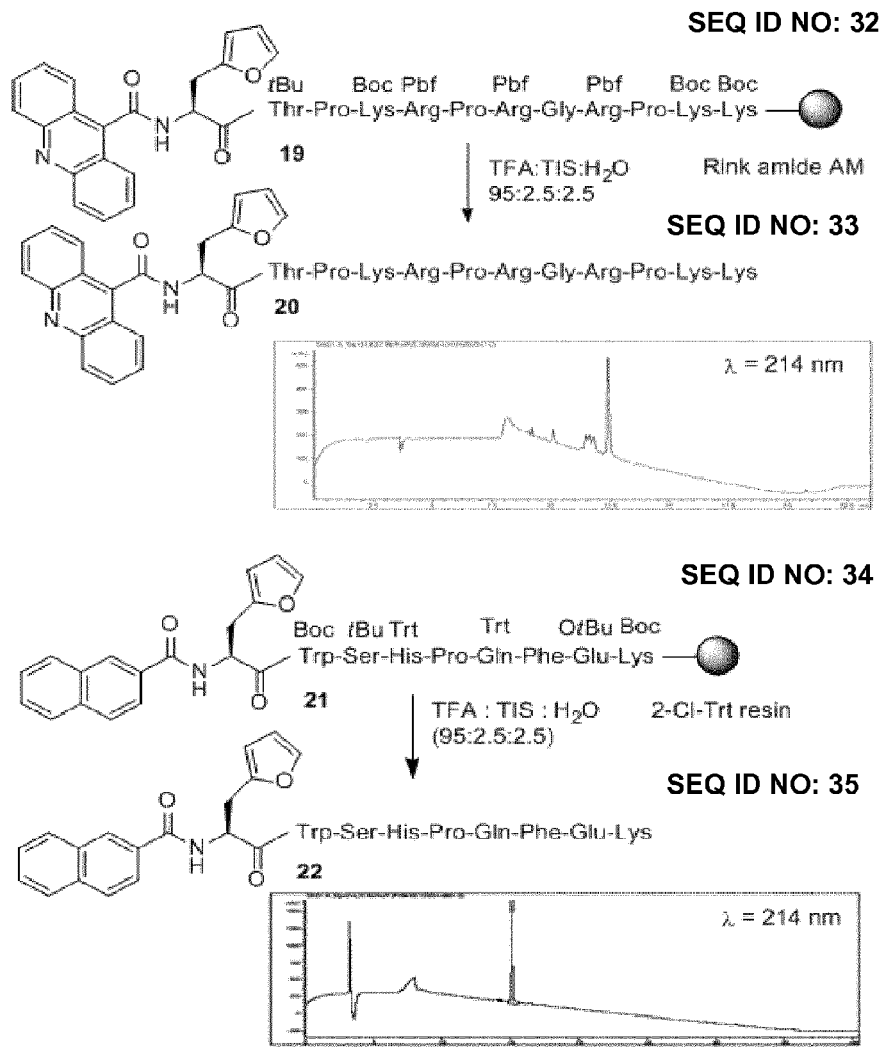
FIG. 22 represents HPLC analysis after the cleavage of two N-terminal furan-peptides with TFA, TIS and water.

As shown in FIG. 22, two N-terminal furan-peptides were prepared with an N-terminal (2-furyl)-alanine which was capped with an aromatic moiety. The first N-terminal furan-peptide 19 was synthesized on a Rink amide resin and was capped with acridine-9-carboxylic acid. The second N-terminal furan-peptide 21 was synthesized on a 2-chlorotrityl chloride resin and was capped with 2-naphtoic acid. Both peptides 19 and 21 were cleaved from the resin with a cleavage cocktail comprising TFA, TIS and water (95:2.5:2.5). For both peptides 19 and 21, pure products were obtained corresponding to the desired free furan-peptides 20 and 22. The furan moiety remained intact during the acidic cleavage. This unexpected stability of the N-terminal furan-moiety capped with an aromatic moiety can be found in π-π stacking of the aromatic moiety with the furan-moiety. The capping moiety thereby protects the furan ring from degradation.

Therefore, capping of the N-terminal furan amino acid with an aromatic capping moiety in combination with cleavage with a cleavage cocktail comprising TFA, TIS and water (95:2.5:2.5), resulted in substantially pure N-terminal furan-peptides in solution.

Example 11

Synthesis of a Furan Amino Acids of Formula (XId) or a Furan Amino Acid of Formula (XIc)

The synthesis of various furan modified lysines was possible starting from commercial Fmoc-Lys(Boc)-OH (FIG. 23) commonly used for Fmoc solid-phase peptide synthesis. Two furan amino acids with a different linker length namely the furan amino acids of Formula (XId) and the furan amino acid of Formula (XIc) (FIG. 23, (3) and (6) respectively) were synthesized in a three step synthesis which was high yielding and easy to scale up.

Figure 23:
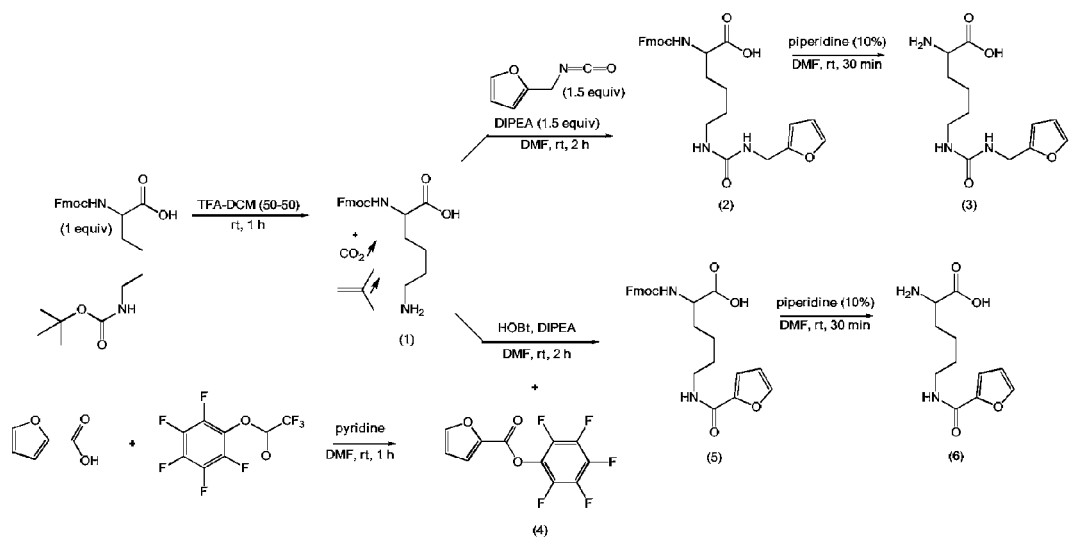
FIG. 23 schematically represents the synthesis of a furan amino acid of Formula (XId) or a furan amino acid of Formula (XIc), starting from a commercially available lysine; (1): Fmoc-Lys-OH; (2): 2-(((((9H-fluoren-9-yl)methoxy)carbonyl)amino)-6-(3-(furan-2-ylmethyl)ureido)hexanoic acid; (3): the furan amino acid of Formula (XId); (4): pentafluorophenyl-furan-2-carboxylate; (5): 2-(((((9H-fluoren-9-yl)methoxy) carbonyl)amino)-6-(furan-2-carboxamido)hexanoic acid; (6): the furan amino acid of Formula (XIc).

After Boc deprotection of the Fmoc-Lys(Boc)-OH, Fmoc-Lys-OH was obtained (FIG. 23, (1)). The furan moiety was coupled to the ε-amine of Fmoc-Lys-OH by ureum formation with furfuryl isocyanate to obtain 2-((((9H-fluoren-9-yl)methoxy)carbonyl)amino)-6-(3-(furan-2-ylmethyl)ureido) hexanoic acid (FIG. 23, (2)), or by amide formation with pentafluorophenyl-furan-2-carboxylate (FIG. 23, (4)) to obtain 2-((((9H-fluoren-9-yl)methoxy)carbonyl)amino)-6-(furan-2-carboxamido)hexanoic acid (FIG. 23, (5)). The synthesis was finished with Fmoc deprotection, yielding the amphiphilic products (3) or (6) (FIG. 23) as a white powder. Hence, the furan amino acid of Formula (XId) or the furan amino acid of Formula (XIc) was obtained (FIG. 23, (3) or (6) respectively).

Example 12

Production of Yellow Fluorescent Protein Comprising a Furan Amino Acid

The incorporation of unnatural furan amino acids by the pyrrolysyl-tRNA synthetase and its tRNA-CUA in Yellow Fluorescent Protein (YFP) can be easily evaluated by monitoring its fluorescence with confocal microscopy. Without incorporation of the furan amino acid at the amber codon position a truncated non-fluorescent protein was obtained, therefore the obtained fluorescence intensity paralleled the incorporation efficiency. The incorporation of the furan amino acids was tested with the tRNA-CUA of *Methanosarcina mazei* (*M. mazei*) and with the wild type pyrrolysyl-tRNA synthetase of *M. mazei* and the Tyr384Phe-Tyr306Ala variant of the pyrrolysyl-tRNA synthetase of *M. mazei* (Yanagisawa et al., Chemistry & Biology, 2008, 15, 1187-1197).

The furan amino acid of Formula (XId) or the furan amino acid of Formula (XIc) was added in a concentration of 0, 2, 5 and 10 mM to 5 ml cell cultures of T7 Express Competent *E. coli* (from New England BioLabs) transformed with a pET-Duet-1 plasmid (Novagen) containing the genes for the pyrrolysine tRNA-synthetase, 3 copies of the tRNA-CUA and the mutated YFP, in LB medium with the appropriate antibiotic. The wild type synthetase did not incorporate the furan amino acid of Formula (XId) in the YFP. However, the furan amino acid of Formula (XIc) was incorporated in YFP by the wild type synthetase in good yield. This result was unexpected in view of the results with the thiophene modified amino acid (Li et al., Journal of Molecular Biology, 2009, 385(4), 1156-64). The mutated pyrrolysine tRNA-synthetase gave lower yields, but incorporated both the furan amino acid of Formula (XId) and the furan amino acid of Formula (XIc) in YFP. The incorporation in YFP of the furan amino acid of Formula (XIc) was better than the incorporation of the furan amino acid of Formula (XId), but in lower yield than with the wild type synthetase.

Example 13

Production of thioredoxinA Comprising a Furan Amino Acid

In addition to YFP, another protein, thioredoxinA (TrxA), was chosen for providing additional proof of incorporation of a furan amino acid in a protein, through mass characterization after purification.

Experiments were performed similar as in Example 12 with wild type pyrrolysyl-tRNA synthetase and tRNA-CUA of *M. mazei*, with the mutated TrxA and with the furan amino acid of Formula (XIc) in a concentration of 5 mM in a 1 l cell culture. This yielded 170 μg of protein after purification over a Strep column. Accurate mass determination with full protein LCMS analysis (Orbitrap, Thermo Scientific) found a mass of 13039.7 Dalton (the calculated average mass of the furan-modified oxidized thioredoxinA without the starting methionine is 13039.95 Dalton), proving the incorporation of the furan amino acid in the protein and its stability. A trypsin digest of the protein and subsequent analysis of the obtained peptides showed incorporation of the furan amino acid on the correct position of TrxA.

The invention claimed is:

1. A method for cross-linking peptides comprising the steps of:
 a) providing a composition comprising furan-peptides, said furan-peptides comprising at least one amino acid comprising a furan-moiety, wherein said furan-peptides are not coupled to a solid support selected from a polystyrene resin comprising an acid labile linker or a polystyrene-co-polyethyleneglycol resin comprising an acid labile linker;
 b) contacting said composition comprising furan-peptides with second peptides, thereby obtaining a mixture comprising furan-peptides and second peptides;
 c) adding an activation signal to said mixture of step b), thereby activating said furan-peptides to activated furan-peptides, and
 d) reacting said activated furan-peptides with said second peptides, thereby cross-linking said activated furan-peptides with said second peptides.

2. The method for cross-linking peptides according to claim 1, wherein said activation signal activates said furan-moiety to an enal-moiety.

3. The method for cross-linking peptides according to claim 1, wherein said activated furan-peptides comprise an enal-moiety.

4. The method for cross-linking peptides according to claim 1, wherein said second peptides comprise at least one amino acid comprising a sulfhydryl group, hydroxyl group, amine group, imidazole group and/or indole group.

5. The method for cross-linking peptides according to claim 4, wherein said enal-moiety of said activated furan-peptides reacts with said sulfhydryl group, hydroxyl group, amine group, imidazole group and/or indole group of said amino acid of said second peptides.

6. The method for cross-linking peptides according to claim 1, further comprising the step of identifying said second peptides cross-linked with said activated furan-peptides of step d).

7. The method for cross-linking peptides according to claim 5, further comprising identifying said amino acid of said second peptides reacted with said enal-moiety of said activated furan-peptides.

8. The method for cross-linking peptides according to claim 7, wherein said amino acid of said second peptide is Cys, Lys, Arg, Ser, Thr, Tyr, His, Trp and/or an N-terminal amino acid.

9. The method for cross-linking peptides according to claim 1, wherein said activation signal is selected from the group consisting of chemical oxidants, enzymes and singlet oxygen.

10. The method for cross-linking peptides according to claim 9, wherein said chemical oxidants are selected from the group consisting of NBS (N-bromo-succinimide), NaOCl, $H_2O_2$ and peracids.

11. The method for cross-linking peptides according to claim 9, wherein said enzymes belong to the class of cytochrome P450 enzymes.

12. The method for cross-linking peptides according to claim 1, wherein said composition comprises at least 60%, 65%, 70%, 75%, 80%, 85%, 90%, 95%, 96%, 97%, 98%, 99% or 100% furan-peptides.

13. The method for cross-linking peptides according to claim 1, wherein prior to step (a), furan-peptides are produced by incorporating at least one furan amino acid into a peptide during solid-phase peptide synthesis (SPPS) of said peptide.

14. The method for cross-linking peptides according to claim 1, wherein prior to step (a), furan-peptides comprising an N-terminal furan-moiety are produced by a method comprising the steps of:
  synthesizing peptides by coupling amino acids via amide bonds on a solid support, wherein at least the N-terminal amino acid comprises a furan-moiety, thereby obtaining furan-peptides coupled to a solid support comprising an N-terminal furan-moiety;
  capping the N-terminal amino acid of said furan-peptides comprising an N-terminal furan-moiety with a capping moiety, thereby obtaining capped furan-peptides comprising an N-terminal furan-moiety; and
  cleaving in solution said capped furan-peptides comprising an N-terminal furan-moiety from said solid support, thereby producing cleavage products in solution, wherein at least 60% of said cleavage products in solution are furan-peptides.

15. The method for cross-linking peptides according to claim 14, wherein said capping moiety is an aromatic moiety.

16. The method for cross-linking peptides according to claim 1, wherein prior to step (a), furan-peptides are produced by incorporating at least one furan amino acid into a peptide during peptide translation in prokaryotes or in eukaryotes.

17. The method for cross-linking peptides according to claim 1, wherein prior to step (a) furan-peptides are produced by a method comprising the steps of:
  providing a translation system comprising: (i) a furan amino acid, (ii) an orthogonal pyrrolysyl-tRNA synthetase of *Methanosarcina mazei*, or a functional fragment or variant thereof, (iii) an orthogonal tRNA-CUA of *Methanosarcina mazei*, wherein said orthogonal tRNA-CUA is specifically aminoacylated by said orthogonal pyrrolysyl-tRNA synthetase with the furan amino acid, and (iv) a nucleic acid encoding a peptide, wherein the nucleic acid comprises a codon that is recognized by said orthogonal tRNA-CUA; and
  translating the nucleic acid, thereby incorporating the furan amino acid into the peptide.

18. The method according to claim 16, wherein said furan amino acid is selected from a furan amino acid of Formula (XIa), (XIb) or (XIc), or a stereoisomeric form thereof, wherein X is selected from NH, O, S or P

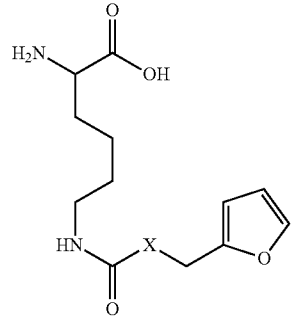

(XIa)

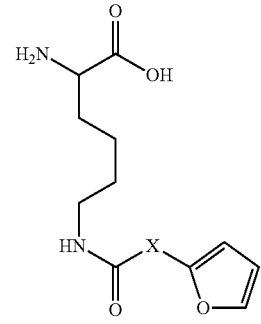

(XIb)

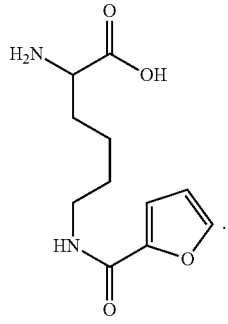

(XIc)

19. A method for identifying a binding site of two interacting peptides comprising steps a) to d) of the method of claim 1, wherein said amino acid comprising a furan-moiety is located at position n of said furan-peptides; said method further comprises the steps of:
  e) determining the cross-link of said furan-peptides and said second peptides;
  f) identifying said amino acid comprising a furan-moiety at position n as being a binding site of said two interacting peptides if cross-linking is detected; and
  g) optionally repeating steps a) to f) with said furan-peptides, wherein said amino acid comprising a furan-moiety is located at position n+p of said furan-peptides; wherein position n may be any amino acid of said furan-peptides; and wherein p is a positive or negative integer (provided position n+p is located on said furan-peptides).

20. A method for identifying a binding site of two interacting peptides comprising the steps of:
   a) providing a composition comprising furan-peptides, said furan-peptides comprising at least one amino acid comprising a furan-moiety, and wherein said amino acid comprising a furan-moiety is located at position n of said furan-peptides;
   b) contacting said composition comprising furan-peptides with second peptides, thereby obtaining a mixture comprising furan-peptides and second peptides;
   c) adding an activation signal to step b), thereby activating said furan-peptides to activated furan-peptides;
   d) reacting said activated furan-peptides with said second peptides, thereby cross-linking said activated furan-peptides with said second peptides;
   e) determining the cross-link of said interacting peptides;
   f) identifying said amino acid comprising a furan-moiety as a binding site of two interacting peptides if cross-linking is detected; and
   g) optionally repeating steps a) to f) with said furan-peptides, wherein said amino acid comprising a furan-moiety is located at position n+p of said furan-peptides; wherein position n may be any amino acid of said furan-peptides;
   and wherein p is a positive or negative integer (provided position n+p is located on said furan-peptides).

21. A method for producing furan-peptides comprising an N-terminal furan-moiety comprising the steps of:
   synthesizing peptides by coupling amino acids via amide bonds on a solid support, wherein at least the N-terminal amino acid comprises a furan-moiety, thereby obtaining furan-peptides coupled to a solid support comprising an N-terminal furan-moiety;
   capping the N-terminal amino acid of said furan-peptides comprising an N-terminal furan-moiety with a capping moiety, thereby obtaining capped furan-peptides comprising an N-terminal furan-moiety; and
   cleaving in solution said capped furan-peptides comprising an N-terminal furan-moiety from said solid support, thereby producing cleavage products in solution, wherein at least 60% of said cleavage products in solution are furan-peptides.

22. The method according to claim 21, wherein said capping moiety is an aromatic moiety.

23. A method for producing furan-peptides comprising the step of incorporating at least one furan amino acid into a peptide during peptide translation in prokaryotes or in eukaryotes, wherein said furan amino acid is selected from a furan amino acid of Formula (XIa), (XIb) or (XIc), or a stereoisomeric form thereof, and wherein X is selected from NH, O, S or P

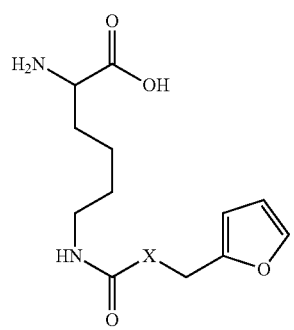
(XIa)

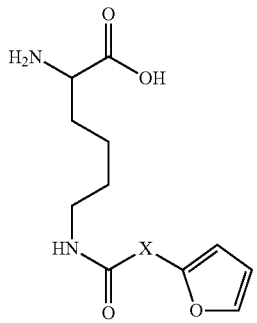
(XIb)

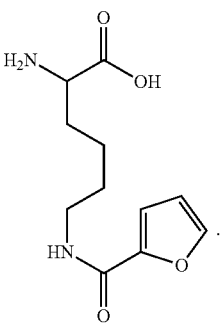
(XIc)

24. The method according to claim 23, further comprising the steps of:

providing a translation system comprising: (i) said furan amino acid, (ii) an orthogonal pyrrolysyl-tRNA synthetase of *Methanosarcina mazei*, or a functional fragment or variant thereof, (iii) an orthogonal tRNA-CUA of *Methanosarcina mazei*, wherein said orthogonal tRNA-CUA is specifically aminoacylated by said orthogonal pyrrolysyl-tRNA synthetase with said furan amino acid, and (iv) a nucleic acid encoding a peptide, wherein the nucleic acid comprises a codon that is recognized by said orthogonal tRNA-CUA; and translating said nucleic acid, thereby incorporating said furan amino acid into said peptide.

25. A furan amino acid of Formula (XIa), (XIb) or (XIc), or a stereoisomeric form thereof, wherein X is selected from NH, O, S or P

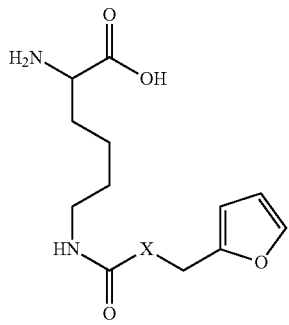
(XIa)

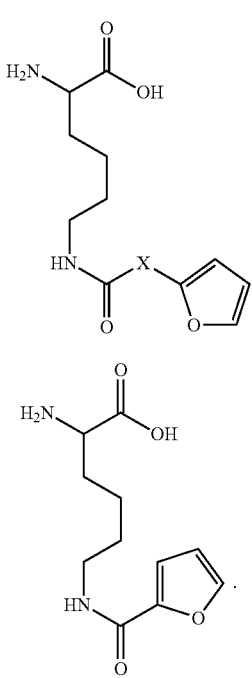

(XIb)

(XIc)

26. Free furan-peptides comprising an N-terminal furan-moiety obtainable by the method according to claim 21.

27. The method according to claim 6, wherein identifying said second peptides cross-linked with said activated furan-peptides is performed by at least one technique selected from the group consisting of: liquid chromatography-mass spectrometry (LC-MS), gel-electrophoresis analysis, matrix-assisted laser desorption/ionization-time of flight (MALDI-TOF), and electro spray ionization-mass spectrometry (ESI-MS).

28. The method according to claim 7, wherein identifying said amino acid of said second peptides reacted with said enal-moiety of said activated furan-peptides is performed by at least one technique selected from the group consisting of: liquid chromatography-mass spectrometry (LC-MS), gel-electrophoresis analysis, matrix-assisted laser desorption/ionization-time of flight (MALDI-TOF) or electro spray ionization-mass spectrometry (ESI-MS).

* * * * *

SEQUENCE LISTING

<160> NUMBER OF SEQ ID NOS: 35

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Trp Ser His Pro Gln Phe Glu Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Furan-Ala

<400> SEQUENCE: 2

Ala Trp Ser His Pro Gln Phe Glu Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Furan-Ala

<400> SEQUENCE: 3

Trp Ser His Pro Gln Phe Glu Lys Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Furan-Ala

<400> SEQUENCE: 4

Trp Ser His Pro Gln Phe Glu Ala
1               5

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 5

Val Glu Asp Arg Thr Val Asp Val His Ile Arg Arg Leu Arg Lys Ala
1               5                   10                  15

Leu Glu Pro Gly
            20

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala His Asn Leu Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Furan-Ala

<400> SEQUENCE: 7

Leu Ala Gly Lys Val
1               5

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Lys Val
1

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Glu Asp Arg Thr Val Asp Val His Ile Arg Arg Leu Arg Lys Ala
1               5                   10                  15

Leu Glu Pro Gly
            20

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Thr Val Asp Val His Ile Arg Arg Leu Arg Lys Ala Leu Glu Pro Gly
1               5                   10                  15

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Glu Asp Thr Val Asp
1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ile Arg Arg Leu Arg Lys Ala Leu Glu Pro Gly
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Glu Asp Arg Thr Val Asp Val
1               5

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Arg Arg Leu Arg Lys Ala Leu Glu Pro Gly
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Glu Asp Arg Thr Val Asp Val His Ile Arg
1               5                   10

<210> SEQ ID NO 16
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Arg Lys Ala Leu Glu Pro Gly
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Pro Lys Arg Pro Arg Gly Arg Pro Lys Lys
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Ser His Pro Gln Phe Glu Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Trp Arg His Pro Gln Phe Gly Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp(Boc)
<220> FEATURE:
<221> NAME/KEY: MOD_RES
<222> LOCATION: (2)..(2)
<223> OTHER INFORMATION: Ser(tBu)
<220> FEATURE:
<221> NAME/KEY: MOD_RES
<222> LOCATION: (3)..(3)
<223> OTHER INFORMATION: His(Trt)
<220> FEATURE:
<221> NAME/KEY: MOD_RES
<222> LOCATION: (5)..(5)
<223> OTHER INFORMATION: Gln(Trt)
<220> FEATURE:
<221> NAME/KEY: MOD_RES
```

```
<222> LOCATION: (7)..(7)
<223> OTHER INFORMATION: Glu(OtBu)
<220> FEATURE:
<221> NAME/KEY: MOD_RES
<222> LOCATION: (8)..(8)
<223> OTHER INFORMATION: Lys(Boc)

<400> SEQUENCE: 20

Trp Ser His Pro Gln Phe Glu Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Furan-Ala
<220> FEATURE:
<221> NAME/KEY: MOD_RES
<222> LOCATION: (2)..(2)
<223> OTHER INFORMATION: Trp(Boc)
<220> FEATURE:
<221> NAME/KEY: MOD_RES
<222> LOCATION: (3)..(3)
<223> OTHER INFORMATION: Ser(tBu)
<220> FEATURE:
<221> NAME/KEY: MOD_RES
<222> LOCATION: (4)..(4)
<223> OTHER INFORMATION: His(Trt)
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (8)..(8)
<223> OTHER INFORMATION: Glu(OtBu)
<220> FEATURE:
<221> NAME/KEY: MOD_RES
<222> LOCATION: (9)..(9)
<223> OTHER INFORMATION: Lys(Boc)

<400> SEQUENCE: 21

Ala Trp Ser His Pro Gln Phe Glu Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trp(Boc)
<220> FEATURE:
<221> NAME/KEY: MOD_RES
<222> LOCATION: (2)..(2)
<223> OTHER INFORMATION: Ser(tBu)
<220> FEATURE:
<221> NAME/KEY: MOD_RES
<222> LOCATION: (3)..(3)
<223> OTHER INFORMATION: His(Trt)
<220> FEATURE:
<221> NAME/KEY: MOD_RES
<222> LOCATION: (5)..(5)
<223> OTHER INFORMATION: Gln(Trt)
<220> FEATURE:
```

```
<221> NAME/KEY: MOD_RES
<222> LOCATION: (7)..(7)
<223> OTHER INFORMATION: Glu(OtBu)
<220> FEATURE:
<221> NAME/KEY: MOD_RES
<222> LOCATION: (8)..(8)
<223> OTHER INFORMATION: Lys(Boc)
<220> FEATURE:
<221> NAME/KEY: MOD_RES
<222> LOCATION: (9)..(9)
<223> OTHER INFORMATION: Furan-Ala

<400> SEQUENCE: 22

Trp Ser His Pro Gln Phe Glu Lys Ala
1               5

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu(tBu)
<220> FEATURE:
<221> NAME/KEY: MOD_RES
<222> LOCATION: (3)..(3)
<223> OTHER INFORMATION: Asp(tBu)
<220> FEATURE:
<221> NAME/KEY: MOD_RES
<222> LOCATION: (4)..(4)
<223> OTHER INFORMATION: Arg(Pbf)
<220> FEATURE:
<221> NAME/KEY: MOD_RES
<222> LOCATION: (5)..(5)
<223> OTHER INFORMATION: Thr(tBu)
<220> FEATURE:
<221> NAME/KEY: MOD_RES
<222> LOCATION: (7)..(7)
<223> OTHER INFORMATION: Asp(tBu)
<220> FEATURE:
<221> NAME/KEY: MOD_RES
<222> LOCATION: (9)..(9)
<223> OTHER INFORMATION: His(Trt)
<220> FEATURE:
<221> NAME/KEY: MOD_RES
<222> LOCATION: (11)..(11)
<223> OTHER INFORMATION: Arg(Pbf)
<220> FEATURE:
<221> NAME/KEY: MOD_RES
<222> LOCATION: (12)..(12)
<223> OTHER INFORMATION: Arg(Pbf)
<220> FEATURE:
<221> NAME/KEY: MOD_RES
<222> LOCATION: (14)..(14)
<223> OTHER INFORMATION: Arg(Pbf)
<220> FEATURE:
<221> NAME/KEY: MOD_RES
<222> LOCATION: (15)..(15)
<223> OTHER INFORMATION: Lys(Boc)
<220> FEATURE:
<221> NAME/KEY: MOD_RES
<222> LOCATION: (18)..(18)
<223> OTHER INFORMATION: Glu(tBu)

<400> SEQUENCE: 23

Val Glu Asp Arg Thr Val Asp Val His Ile Arg Arg Leu Arg Lys Ala
1               5                   10                  15

Leu Glu Pro Gly
            20
```

```
<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: His(Trt)
<220> FEATURE:
<221> NAME/KEY: MOD_RES
<222> LOCATION: (3)..(3)
<223> OTHER INFORMATION: Asn(Trt)

<400> SEQUENCE: 24

Ala His Asn Leu Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu(Fmoc)
<220> FEATURE:
<221> NAME/KEY: MOD_RES
<222> LOCATION: (2)..(2)
<223> OTHER INFORMATION: Furan-Ala
<220> FEATURE:
<221> NAME/KEY: MOD_RES
<222> LOCATION: (4)..(4)
<223> OTHER INFORMATION: Lys(Boc)

<400> SEQUENCE: 25

Leu Ala Gly Lys Val
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Leu(Fmoc)
<220> FEATURE:
<221> NAME/KEY: MOD_RES
<222> LOCATION: (2)..(2)
<223> OTHER INFORMATION: Furan modified amino acid

<400> SEQUENCE: 26

Leu Xaa Gly Lys Val
1               5

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (21)..(21)
<223> OTHER INFORMATION: Furan-Ala

<400> SEQUENCE: 27

Val Glu Asp Arg Thr Val Asp Val His Ile Arg Arg Leu Arg Lys Ala
1               5                   10                  15

Leu Glu Pro Gly Ala
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Furan-Ala

<400> SEQUENCE: 28

Val Glu Asp Ala Thr Val Asp Val His Ile Arg Arg Leu Arg Lys Ala
1               5                   10                  15

Leu Glu Pro Gly
            20

<210> SEQ ID NO 29
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Furan-Ala

<400> SEQUENCE: 29

Val Glu Asp Arg Thr Val Asp Ala His Ile Arg Arg Leu Arg Lys Ala
1               5                   10                  15

Leu Glu Pro Gly
            20

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Furan-Ala

<400> SEQUENCE: 30

Val Glu Asp Arg Thr Val Asp Val Ala Ile Arg Arg Leu Arg Lys Ala
1               5                   10                  15

Leu Glu Pro Gly
            20

<210> SEQ ID NO 31
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Furan-Ala

<400> SEQUENCE: 31

Val Glu Asp Arg Thr Val Asp Val His Ile Arg Ala Leu Arg Lys Ala
1               5                   10                  15

Leu Glu Pro Gly
            20

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Furan-Ala
<220> FEATURE:
<221> NAME/KEY: MOD_RES
<222> LOCATION: (2)..(2)
<223> OTHER INFORMATION: Thr(tBu)
<220> FEATURE:
<221> NAME/KEY: MOD_RES
<222> LOCATION: (4)..(4)
<223> OTHER INFORMATION: Lys(Boc)
<220> FEATURE:
<221> NAME/KEY: MOD_RES
<222> LOCATION: (5)..(5)
<223> OTHER INFORMATION: Arg(Pbf)
<220> FEATURE:
<221> NAME/KEY: MOD_RES
<222> LOCATION: (7)..(7)
<223> OTHER INFORMATION: Arg(Pbf)
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (11)..(11)
<223> OTHER INFORMATION: Lys(Boc)
<220> FEATURE:
<221> NAME/KEY: MOD_RES
<222> LOCATION: (12)..(12)
<223> OTHER INFORMATION: Lys(Boc)

<400> SEQUENCE: 32

Ala Thr Pro Lys Arg Pro Arg Gly Arg Pro Lys Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Furan-Ala

<400> SEQUENCE: 33

Ala Thr Pro Lys Arg Pro Arg Gly Arg Pro Lys Lys
1               5                   10
```

```
<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Furan-Ala
<220> FEATURE:
<221> NAME/KEY: MOD_RES
<222> LOCATION: (2)..(2)
<223> OTHER INFORMATION: Trp(Boc)
<220> FEATURE:
<221> NAME/KEY: MOD_RES
<222> LOCATION: (3)..(3)
<223> OTHER INFORMATION: Ser(tBu)
<220> FEATURE:
<221> NAME/KEY: MOD_RES
<222> LOCATION: (4)..(4)
<223> OTHER INFORMATION: His(Trt)
<220> FEATURE:
<221> NAME/KEY: MOD_RES
<222> LOCATION: (6)..(6)
<223> OTHER INFORMATION: Gln(Trt)
<220> FEATURE:
<221> NAME/KEY: MOD_RES
<222> LOCATION: (8)..(8)
<223> OTHER INFORMATION: Glu(OtBu)
<220> FEATURE:
<221> NAME/KEY: MOD_RES
<222> LOCATION: (9)..(9)
<223> OTHER INFORMATION: Lys(Boc)

<400> SEQUENCE: 34

Ala Trp Ser His Pro Gln Phe Glu Lys
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Furan-Ala

<400> SEQUENCE: 35

Ala Trp Ser His Pro Gln Phe Glu Lys
1               5
```